(12) United States Patent
Maria et al.

(10) Patent No.: US 8,440,795 B2
(45) Date of Patent: May 14, 2013

(54) KUNITZ-TYPE RECOMBINANT INHIBITOR

(75) Inventors: Durvanei Augusto Maria, São Paulo (BR); Ana Marisa Chudzinski-Tavassi, São Paulo (BR); Isabel De Fatima Correia Batista, São Paulo (BR); Paulo Lee Ho, São Paulo (BR)

(73) Assignee: Coinfair-Consórcio De Indústrias Farmacêuticas, São Paulo (BR)

( * ) Notice: Subject to any disclaimer, the term of this patent is extended or adjusted under 35 U.S.C. 154(b) by 716 days.

(21) Appl. No.: 11/724,557

(22) Filed: Mar. 14, 2007

(65) Prior Publication Data

US 2009/0042786 A1    Feb. 12, 2009

Related U.S. Application Data

(63) Continuation-in-part of application No. PCT/BR2005/000185, filed on Sep. 15, 2005.

(30) Foreign Application Priority Data

Sep. 15, 2004 (BR) ..................... 0406057

(51) Int. Cl.
```
C07K 14/00    (2006.01)
A61K 38/16    (2006.01)
A61K 35/64    (2006.01)
A61P 7/02     (2006.01)
A61P 35/00    (2006.01)
A61P 35/04    (2006.01)
```
(52) U.S. Cl.
USPC ........... 530/350; 514/1.1; 514/13.5; 514/19.3

(58) Field of Classification Search .................. None
See application file for complete search history.

(56) References Cited

FOREIGN PATENT DOCUMENTS

| AU | 2005284615 | 3/2006 |
|---|---|---|
| BR | PI0406057-1 | 9/2004 |
| CA | 2581001 | 3/2006 |
| CN | 101142232 | 3/2008 |
| EP | 034561 | 6/1994 |
| EP | 1799707 | 6/2007 |
| JP | 2008512992 | 5/2008 |
| WO | 2006029492 | 3/2006 |

OTHER PUBLICATIONS

Yuan, S-M., et al. 1998 Proteins 30: 136-143.*
Sergel, T.A., et al. 2000 Journal of Virology 74(11): 5101-5107.*
Bergqvist, "Venous thromboembolism in cancer patients: expanding horizons," *Seminars in Thrombosis and Hemostasis* 28 (Suppl. 3):19-23 (2002).
Broze, "Tissue factor pathway inhibitor gene disruption," *Blood Coagulation and Fibrinolysis* 9 (Suppl. 1):S89-S92 (1998).
Chand et al., "Structure-function analysis of the reactive site in the first kunitz-type domain of human tissue factor pathway inhibitor-2," *The Journal of Biological Chemistry* 279:17500-17507 (2004).

Contrino et al., "In situ detection of expression of tissue factor in vascular endothelial cells: correlation with the malignant phenotype of human breast disease," *Nature Medicine* 2:209-215 (1996).
DeClerck et al., "Protease inhibitors: role and potential therapeutic use in human cancer," *European Journal of Cancer* 30A:2170-2180 (1994).
Edwards et al., "Human tumor procoagulation," *Thrombosis and Haemostasis* 69:205-213 (1993).
Fernandez et al., "Tissue factor and fibrin in tumor angiogenesis," *Seminars in Thrombosis and Hemostasis* 30:31-44 (2004).
Francishetti et al., "Ixolaris, a novel recombinant tissue factor pathway inhibitor (TFPI) from the salivary gland of the tick, *Ixodes scapularis*: identification of factor X and factor Xa as scaffolds for the inhibition of factor VIIa/tissue factor complex," *Blood* 99(10):3602-3612 (2002).
Gale et al., "Update on tumor cell procoagulant factors," *Acta Haematologica* 106:25-32 (2001).
Gordon, "Cancer cell procoagulants and their implications," *Hematology/Oncology Clinics of North America* 6:1359-1374 (1992).
Gouin-Thibaut et al., "Venous thrombosis and cancer," *Annales de Biologie Clinique* 58:675-682 (2000).
Greaves, "Dying for a living," In *Cancer: The Evolutionary Legacy* pp. 195-203 (2000).
Hoffman et al., "Cancer and thrombosis revisited," *Blood Reviews* 15:61-67 (2001).
Kamei et al., "Inhibitory properties of human recombinant Arg24->Gln type-2 tissue factor pathway inhibitor (R24Q TFPI-2)," *Thrombosis Research* 94:147-152 (1999).
Lee et al., "Venous thromboembolism and cancer: risks and outcomes," *Circulation* 107(23 Suppl 1):I17-21 (2003).
Loreto et al., "Coagulation and cancer: implications for diagnosis and management," *Pathology Oncology Research* 6:301-312 (2000).
Mousa, "Antithrombotics in thrombosis and cancer," *Expert Review in Cardiovascular Therapy* 1:283-291 (2003).
Ornstein et al., "Cancer, thrombosis, and anticoagulants," *Current Opinion in Pulmonary Medicine* 6:301-308 (2000).
Rao et al.., "Tissue factor residues Lys165 and Lys166 are essential for rapid formation of the quaternary complex of tissue factor. VIIa with Xa.tissue factor pathway inhibitor," *Biochemistry* 34:10867-10871 (1995).
Ribeiro, "Blood-feeding arthropods: live syringes or invertebrate pharmacologists?" *Infectious Agents and Diseases* 4:143-152 (1995).
RicKels et al., "Hemostatic alterations in cancer patients," *Cancer Metastasis Reviews* 11:237-248 (1992).
Sandset et al., "Tissue factor pathway inhibitor: clinical deficiency states," *Thrombosis Haemostasis* 78:467-470 (1997).
Schafer et al., "Thrombotic disorders: diagnosis and treatment," *Hematology Am Soc Hematol Educ Program* pp. 520-539 (2003).
Sorensen et al., "Antiapoptotic effect of coagulation factor VIIa," *Blood* 102:1708-1715 (2003).
Sorensen et al., "Cancer and venous thromboembolism: a multidisciplinary approach," *Clinical Laboratory* 49:615-623 (2003).

(Continued)

*Primary Examiner* — Marsha Tsay
(74) *Attorney, Agent, or Firm* — Fish & Richardson P.C.

(57) ABSTRACT

The present invention presents a Kunitz-type recombinant inhibitor obtained from a gene cloned from a cDNA library of salivary glands of the *Amblyomma cajennense*, and the inhibitor named Amblyomin-X has molecular mass of 13,500 Da.

36 Claims, 25 Drawing Sheets

OTHER PUBLICATIONS

Sutherland et al., "Thromboembolic complications of cancer: epidemiology, pathogenesis, diagnosis, and treatment," *American Journal of Hematology* 72:43-52 (2003).

Zacharski et al., "Pathways of coagulation/fibrinolysis activation in malignancy," *Seminars in Thrombosis and Hemostasis* 18:104-116 (1992).

Zacharski, "Malignancy as a solid-phase coagulopathy: implications for the etiology, pathogenesis, and treatment of cancer," *Seminars in Thrombosis and Hemostasis* 29:239-246 (2003).

* cited by examiner 1    2    3    4

01 02 03 04 05 06 07 08 09 10 11 12 13 14 15 16 17 18

FIGURE 4 caggaaaacgttgcactcagaaatgcgccaacttgccgttctagcgct
cgtaatcttcacgggcatgtgtgttgaatcacagtcggcgaacagcaa
ggcagtttgcaacttgcccaagcttgcgggagacgaaacatgcagcaa
caaaactgagattcgctggtattacaacggaacggcttgcgaagcttt
catattcaagggctgtggtggaaacgacaataatttcgacagggtcga
cgactgccaaaggctgtgtgaggagcaaacactttcacttcgagtc
accgaaattgatttgtttcaaagtacaggactattggatactaaacga
tattatgaagaaaaacctcactggaatttccctaaaaagtgaggaaga
ggatgcagattctggagaaattgattgagtttgaagcaattgattgag
tttgaagaatgtactttaataaacttctttaaaatcaaaaaaaaaaa
aaaaaaaaaaaaaaaaaaaaaaa

FIGURE 5

```
1           11          21          31
MRQLAVLALV  IFTGMCVESQ  SANSKAVCNL  PKLAGDETCS 41          51          61          71
NKTEIRWYYN  GTACEAFIFK  GCGGNDNNFD  RVDDCQRLCE 81          91          101         111
EQTHFHFESP  KLICFKVQDY  WILNDIMKKN  LTGISLKSEE

121
EDADSGEID
```

FIGURE 6

```
1           11          21          31
ANSKAVCNLP  KLAGDETCSN  KTEIRWYYNG  TACEAFIFKG
41          51          61          71
CGGNDNNFDR  VDDCQRLCEE  QTHFHFESPK  LICFKVQDYW
81          91          101
ILNDIMKKNL  TGISLKSEEE  DADSGEID
```

CTC GAG GCG AAC AGC AAG GCA GTT TGC

FIGURE 9

```
                                    10        20        30        40
Amblyomin-X   AN-----------SKAVCNLPKLAGDETCSNKTEIRWYYNGTA--CEAFIFKGCGGNDNN
                          :.           : . :  :..    :: ..    . ::  .
              ::     :::..:.
Ixolaris      AERVSEMDIYEFESWVSCLDPEQV---TCESQEGTHASYNRKTGQCEEQKGTECGGGENH
                        10        20        30        40        50

50        60        70        80        90
Amblyomin-X   FDRVDDCQRLCEEQTHFHFESPKLICFKVQDY---------WIL--NDIMKKNLT--GIS
                       :.. :.. :..          .::  :      ::             :
              :.   . .:  ::..
Ixolaris      FETLLKCNESCND-------APKPPCSLEVDYGVGRANIPRWYYDTNNATCEMFTYGGIT
                        60        70        80        90        100       110

100
Amblyomin-X   -----LKSEEEDADSGE-----------ID
                   ..::::  ... .              :.
Ixolaris      GNKNNFESEEECKETCKGFSLLKKVNVTIN
                        120       130       140
```

FIGURE 10
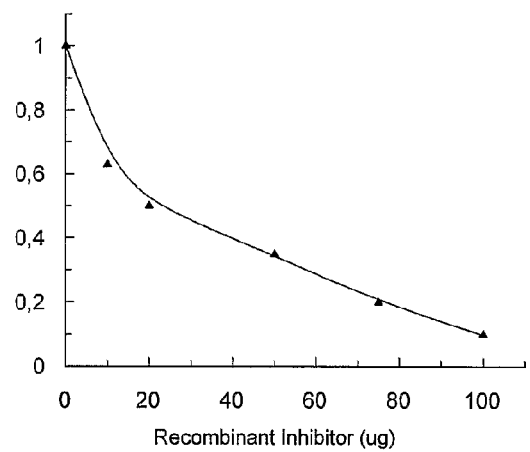
FIGURES 11A and 11B
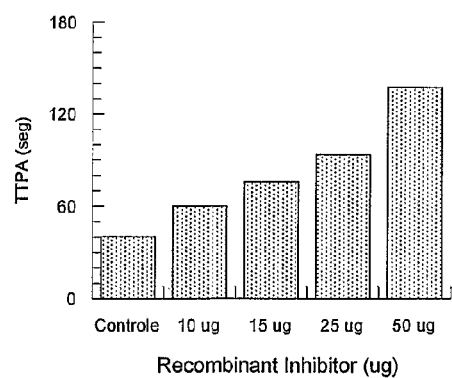
A
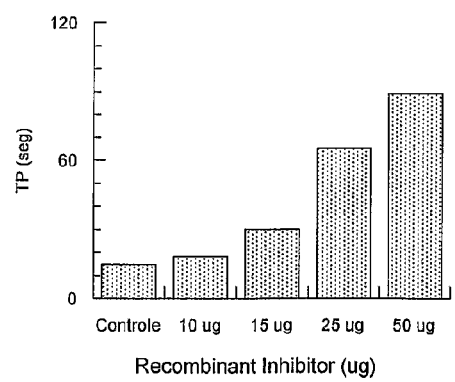
B

Zoom 200X

Zoom 200X

A-Control    B Amblyomin-X

Zoom 200X

FIGURE 24

FIGURE 25
FIGURE 25A
FIGURE 25B

SEQUENCE LISTING

```
<160> NUMBER OF SEQ ID NOS: 6

<210> SEQ ID NO 1
<211> LENGTH: 504
<212> TYPE: DNA
<213> ORGANISM: Amblyomma cajennense

<400> SEQUENCE: 1
caggaaaacg ttgcactcag aaatgcgcca acttgccgtt ctagcgctcg taatcttcac      60
gggcatgtgt gttgaatcac agtcggcgaa cagcaaggca gtttgcaact tgcccaagct     120
tgcgggagac gaaacatgca gcaacaaaac tgagattcgc tggtattaca acggaacggc     180
ttgcgaagct ttcatattca agggctgtgg tggaaacgac aataatttcg acagggtcga     240
cgactgccaa aggctgtgtg aggagcaaac acactttcac ttcgagtcac cgaaattgat     300
ttgtttcaaa gtacaggact attggatact aaacgatatt atgaagaaaa acctcactgg     360
aatttcccta aaaagtgagg aagaggatgc agattctgga gaaattgatt gagtttgaag     420
caattgattg agtttgaaga atgtacttta ataaacttct ttaaaatcaa aaaaaaaaaa     480
aaaaaaaaaa aaaaaaaaaa aaaa                                            504

<210> SEQ ID NO 2
<211> LENGTH: 129
<212> TYPE: PRT
<213> ORGANISM: Amblyomma cajennense

<400> SEQUENCE: 2

Met Arg Gln Leu Ala Val Leu Ala Leu Val Ile Phe Thr Gly Met Cys
1               5                   10                  15

Val Glu Ser Gln Ser Ala Asn Ser Lys Ala Val Cys Asn Leu Pro Lys
            20                  25                  30

Leu Ala Gly Asp Glu Thr Cys Ser Asn Lys Thr Glu Ile Arg Trp Tyr
        35                  40                  45

Tyr Asn Gly Thr Ala Cys Glu Ala Phe Ile Phe Lys Gly Cys Gly Gly
    50                  55                  60

Asn Asp Asn Asn Phe Asp Arg Val Asp Asp Cys Gln Arg Leu Cys Glu
```

```
                   65                  70                  75                  80
Glu Gln Thr His Phe His Phe Glu Ser Pro Lys Leu Ile Cys Phe Lys
                    85                  90                  95

Val Gln Asp Tyr Trp Ile Leu Asn Asp Ile Met Lys Lys Asn Leu Thr
            100                 105                 110

Gly Ile Ser Leu Lys Ser Glu Glu Asp Ala Asp Ser Gly Glu Ile
        115                 120                 125

Asp

<210> SEQ ID NO 3
<211> LENGTH: 108
<212> TYPE: PRT
<213> ORGANISM: Amblyomma cajennense

<400> SEQUENCE: 3

Ala Asn Ser Lys Ala Val Cys Asn Leu Pro Lys Leu Ala Gly Asp Glu
1               5                   10                  15

Thr Cys Ser Asn Lys Thr Glu Ile Arg Trp Tyr Tyr Asn Gly Thr Ala
            20                  25                  30

Cys Glu Ala Phe Ile Phe Lys Gly Cys Gly Gly Asn Asp Asn Asn Phe
        35                  40                  45

Asp Arg Val Asp Asp Cys Gln Arg Leu Cys Glu Glu Gln Thr His Phe
    50                  55                  60

His Phe Glu Ser Pro Lys Leu Ile Cys Phe Lys Val Gln Asp Tyr Trp
65                  70                  75                  80

Ile Leu Asn Asp Ile Met Lys Lys Asn Leu Thr Gly Ile Ser Leu Lys
                85                  90                  95

Ser Glu Glu Asp Ala Asp Ser Gly Glu Ile Asp
            100                 105

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
ctcgaggcga acagcaaggc agtttgc                                              27

<210> SEQ ID NO 5
<211> LENGTH: 61
<212> TYPE: PRT
<213> ORGANISM: Amblyomma cajennense

<400> SEQUENCE: 5

Ala Asn Ser Lys Ala Val Cys Asn Leu Pro Lys Leu Ala Gly Asp Glu
1               5                   10                  15

Thr Cys Ser Asn Lys Thr Glu Ile Arg Trp Tyr Tyr Asn Gly Thr Ala
            20                  25                  30

Cys Glu Ala Phe Ile Phe Lys Gly Cys Gly Gly Asn Asp Asn Asn Phe
        35                  40                  45

Asp Arg Val Asp Asp Cys Gln Arg Leu Cys Glu Glu Gln
    50                  55                  60

<210> SEQ ID NO 6
<211> LENGTH: 47
<212> TYPE: PRT
<213> ORGANISM: Amblyomma cajennense
```

```
<400> SEQUENCE: 6

Thr His Phe His Phe Glu Ser Pro Lys Leu Ile Cys Phe Lys Val Gln
1               5                   10                  15

Asp Tyr Trp Ile Leu Asn Asp Ile Met Lys Lys Asn Leu Thr Gly Ile
            20                  25                  30

Ser Leu Lys Ser Glu Glu Asp Ala Asp Ser Gly Glu Ile Asp
        35                  40                  45
```

KUNITZ-TYPE RECOMBINANT INHIBITOR

CROSS REFERENCE TO RELATED APPLICATIONS

This application is a continuation-in-part of International Application No. PCT/BR2005/000185, filed on Sep. 15, 2005, which claims benefit of Brazilian application no. PI0406057-1, filed on Sep. 15, 2004, the disclosures of which are incorporated by reference herein in their entireties.

TECHNICAL FIELD

This invention refers to the process for the obtainence of a recombinant protein with inhibiting activity on Factor X activated of blood coagulation; characterized as a Kunitz-type inhibitor, obtained from a cDNA library of salivary glands of the *Amblyomma cajennense* tick; to the process for the obtainence of the clone oligonucleotide sequence and the amino acid sequence of the recombinant protein, to the process for determining the inhibiting activity of this recombinant protein on Factor X activated, to the process for determining the anti-coagulant activity in plasma, to the process for determining the apoptotic activity in lineage of tumoral cells, to the process for determining the anti-metastatic activity in melanoma tumor, to the process for determining the anti-cancer activity (melanoma, colon, breast, lungs and leukemia), in vitro and in vivo.

BACKGROUND OF THE INVENTION

Proteinase inhibitors are molecules acting in normal control mechanisms of the proteolytic enzyme activity and are related to many physiological processes as for example coagulation, fibrinolysis, digestion and also in pathologies as cancer, hemorrhagic disturbances, inflammation and blood pressure balance (DECLERCK & IMREM, 1994).

One of the most efficient means for controlling coagulation is the action of proteinase inhibitors. Studies have demonstrated that salivary glands of the majority of the hematophages species as ticks for instance, produce several anti-coagulant substances aiming to turn blood more fluid then optimizing its feeding. (RIBEIRO, 1995).

The inhibitors of Factor X activated (FXa) are of great clinical interest, since through FXa inhibition (in the prothrombinase complex) the control of the activation of the prothrombin into thrombin is possible avoiding clot formation.

The inhibition of proteases is trigged as soon as starts the coagulation process. The "Tissue Factor Pathway Inhibitor" (TFPI) is the main inhibitor of the extrinsic path and was classified as a member of the Kunitz family inhibitors of BPTI (Bovine Pancreatic Trypsin Inhibitor) type (Broze, 1998).

The human TFPI is a protein composed of three Kunitz-type domains (K1, K2 and K3), and K1, the first domain, has an acid region at the N-terminus portion where the binding site to the FVIIa is placed. In the second domain we can find the area responsible for the FXa binding and finally the third domain presents a basic region at its C-terminus portion of which function has not yet been elucidated but probably contains a heparin binding site (Rao, 1995).

The human TFPI inhibition mechanism comprehends two phases. In the first phase the inhibitor associates itself to factors FXa and FVIIa, however the inhibition will really occur in the following phase where a formation of a quaternary complex is seen with the presence of Tissue Factor (TF), FXa, FVIIa and human TFPI (TFPI: FXa: FVIIa: TF) (Sandset & Bendz, 1997).

The inhibitor of the human tissue factor type-2 "tissue factor pathway inhibitor-2" (TFPI-2), is a protein of 32-kDa consisting in three Kunitz-type domains (Chand et. al., 2004). TFPI-2 inhibits a variety of serine proteases involved in coagulation and fibrinolysis probably due to the arginine residue found in the position 24 (R24) of the first Kunitz-type domain. In the second and third domains residues of glutamin and serine respectively can be found. In recent studies a mutant was built where the arginine residue was modified by a glutamin residue (R24Q TFPI-2) and this mutation originates around 90% of the inhibiting activity loss on bovine trypsin. This fact demonstrates the importance of this residue in maintaining the inhibitory activity (Kamei et. al., 1999).

General Aspects of Cancer Development and its Interactions with Coagulation

The risk of a subject developing a neoplasia is determined by a combination of several genetic and environmental factors. Therefore, in the carcinogenesis process, the substance called carcinogen (of biological, chemical or physical natures), can act as starter or even promoter of the process that develops up to the formation of metastases (Ruoslahti E., 1996).

In the starting of the neoplasia process irreversible alterations occur in target structures of the DNA, contributing for the cellular transformation. The carcinogen metabolism is shown in two phases called Phase I (activation) and Phase II (detoxification). Some Phase I enzymes act not only as catalyzer of oxidative reactions, but also metabolizing high quantities of carcinogens or lipophilic xenobiotics (Bell et. al, 1993).

The persistency of the DNA damages depends on repairing mechanisms and on the cellular life lasting of the damaged tissue, that way, if the damage persists or is not repaired, there is an expansion of a mutant cellular clone (Duke et al, 1996; Wainscoat e Fey, 1990).

It is a process, long in many times that occurs on started cells, decreased in latency period and/or increasing their susceptibility to the genetic alterations. Usually the promoters are not genotoxic. They are specific-tissue and have multiple action mechanisms acting in an epigenetic form resulting in tissue homeostasis disturbances (Hermo et al, 1987).

The promotion mechanisms include the activation of cellular surface receptors, activation or inhibition of cytosolic enzymes, activation of transcription and translation factors (by Kinase), proliferation stimulation, apoptosis inhibition, and direct cytotoxicity.

In the progression stage, the tumoral cells also show capacity of forming new blood vessels which will feed them, provoking uncontrolled increasing since they invade tissues around them at first and can be reaching the inside of a lymphatic or blood vessel and through them be spread into other organs. (Meyer et. al., 1998, Matsuda et al 2003).

The cells usually react to several intrinsic damages generated from intermediate metabolism products, from severe or chronic inflammatory reactions and from process causing oxygen and nitrogen unstable reactive metabolites. Besides that, there are extrinsic-damaging factors as for example physical, chemical and biological agents eliminated by homeostatic process.

The last stage, (called tumoral progression), includes invasion and metastasization. In this phase, pre-existing or pre-neoplasia lesions are added to aleatory mutational alterations including aberration of specific-sequence, duplication, deletion and/or loss of heterozygosity in specific genes as oncogenes, tumor suppressor genes, metastogeneses and repairing genes.

Oncogenes are inactive in physiological conditions and can be activate by changing an amino acid, or by the amplification of a gene in a chromosome originating several copies of this gene with the increase of its activity and finally, by the recombination among genes of distinct chromosomes. The difference of these genes is that they are usually active, vigilant for avoiding the uncontrolled growing of the cells (Budillon, 1995).

Although the genomic instability is the main characteristic of the tumoral progression, it is the absence of the control of cellular duplication what distinguishes the malignancy levels and turns them into lethal cancers. The tumoral cells as well as those of a normal tissue duplicate through the cellular cycle (Fearon E R, 1997).

To understand cellular cycle, however, have not completely cleared up the regulation mechanism of the cellular multiplication of tumoral cells and cancers growing characteristics in vivo have not yet been elucidated.

The invasive nature of the tumoral progression is associated to the increase of mobility of tumoral cells, to the proteolysis capacity and to the loss of inhibition of cell-cell and cell-matrix contact. The metastatic cells are then disseminated through the circulatory, lymphatic systems by local extension or even by the implanting process. Therefore, standards for metastasis locations will vary depending on the kind of primary cancer and on organs since some of them like muscles, skin, thymus and spleen will rarely present metastases (Goel, et al., 2004).

Some cancers considered untreatable or without therapeutical response predominantly repeat the place of the primary cancer and in its region lymph nodules. These tumors can also produce metastases during the treatment.

The incidence of malign tumors represents a significant number ranking as the second cause of death in the world. Cancer treatment is based, in general, on surgical removing of solid tumors placed in situ, radiotherapy for tumors in patients without clinical conditions or technical possibilities for its complete removing and chemotherapy for cases of non-solid tumors or of solid tumor spreading.

Chemotherapy, radiotherapy and surgery turned to be therapeutical methods of intensive administration associated with other treatments and introducing the concept of adjuvant treatments has been an innovation in the process of control and cure of many sick patients, improving their results (Tsao, et. al., 2004).

Today, more accurate radiotherapeutical protocols involve the administration of higher doses in tumoral mass, and less intense in healthy adjacent tissues; chemotherapy treatments with efficient drugs on the neoplasia and less side effects allowing wider oncology conducting and consequently more encouraging results for many cases. However, the majority of solid tumors presents modest or inefficient responses to chemotherapy, limiting indications and efficiency both in adjuvant treatment on local tumors and in therapeutical of metastasis cases (Sekire, et al., 2004).

The high incidence of metastases occurring in 50% of patients with advanced lung cancer shows how necessary it is to develop new and more efficient therapeutical strategies aiming to offer to these patients' real opportunities for controlling the proliferation and dissemination of the neoplasia cells.

In the twentieth century we reached an extraordinary advance toward it when new drugs were invented containing wide anti-neoplasia proprieties as the nitrogenated mustard identified in the 40's and a variety of other substances with partial or complete efficacy against some histologic kinds of tumors. Although there is a fast expansion of the anti-cancer drug selection allowing treating several solid tumors like lung, colon, breast and prostate cancers, there has not yet been a systemic treatment proving to be adequate and efficient toward that. In lung carcinomas of non-small cells and in skin melanomas, prevalent in developed countries however frequent all over the world, the modest response when experiencing chemotherapy is from 15% to 20% in all available protocols and from 40% to 50% in other therapeutical associations (Sekire, et al., 2004).

Therefore, searching for new drug alternatives for improving treatment efficacy on advanced neoplasia diseases is vital. The majority of the chemotherapies are known for their capacity of controlling cellular proliferation and drugs with specific activity against some metabolic mechanisms exclusive for tumoral cells (target treatment) were recently identified. In these treatments the substances act against the tumors through cellular cycle alterations allowing being more efficient right in their action mechanisms.

Cancer morbidity related to chemotherapy treatments is still a significant obstacle, therefore, finding anti-neoplasia drugs of easy administration with few or insignificant side effects and selective action mechanisms for the neoplasia cell seems to be a target today.

One of the regulatory routes involved in tumoral growing and progression is the blood coagulation system where primarily this response is caused by the expression of pro-coagulating factors as the Tissue Factor (TF), one of the proteins that trigger the coagulation process leading to thrombin production and clot formation.

At a second phase, tumoral cells come to express the receptor of the urokinase-type plasminogen activator (u-PA) and the plasminogen activators promote the activation of plasminogen into plasmine. This system is responsible for the tissue coordination and remodeling.

In patients with neoplasias as for example pulmonary adenocarcinomas, renal carcinomas and in malign melanoma, there is a loss of homeostasis provoking alterations of the coagulation system, arising from thrombin production and Factor X activated (Edward R L, 1993). On the other hand, the blood coagulation activation occurring in patients with primary neoplasias, or submitted to chemotherapeutic treatments is influenced by the biology of the tumoral cells of which mechanisms have not yet been understood (RicKels et. al., 1992, Schafer, et al., 2003).

The laboratory evaluation of coagulation parameters has shown high levels significant in certain kinds of tumors, turning possible determining it in circulation as for example the presence of prothrombin fragments, of D-dimers, of Factor XIIa and its prognostic correlation (Gordon S G, 1992).

The treatment of patients with primary tumors, metastases or presenting damages during the chemotherapy treatment, with anticoagulants as for example the low molecular weight heparins or K vitamin inhibitors (Hoffmal et al., 2001) showed efficiency in prolonging the life of patients (Moussa et. al., 2003; Sutherland et. al., 2003). The pathogenesis of venous thrombosis in malign neoplasias is multifactorial and its mechanism involves the releasing of pro-coagulant components by the tumor, genetic factors and even of the treatment itself (Sorensen et. al., 2003; Gouin-Thibaut e Samama M M, 2000).

Clinical studies have demonstrated that this thromboembolic feature can be prevented by the use of low molecular weight heparins in breast cancers removed by surgery (Bergqvist D., 2002; Lee e Levine, 2003). The histologic and functional evidences of the interaction of several biological systems as immune system and coagulation in certain neoplasias were identified. They revealed important alterations as the presence of coagulation activating factors associated to the inflammatory infiltrated, to the endothelial cells and the neoangiogeneses (Loreto et. al, 2000; Zacharcki D, 2003; Ornstein et. al, 2000; Gale e Gordon 2001; Cotrino J, 1996).

Cytokines derived from tumoral cells as tumoral necrosis factor (TNF), interleukin 1 and the vascular endothelial growing factor (VEGF), are chemotactic and induce vessel formations since they are able to induce the expression of procoagulant and thrombogenic factors, modifying the procoagulant state at the tumoral micro ambient (Sorensen, et. al, 2003, Fernandez et. al, 2004).

SUMMARY

The disclosure provides nucleic acid sequences that encode polypeptides that can have an anti-coagulation, anti-cancer, pro-apoptotic, anti-metastatic, anti-angiogenic, and/or pro-phagocytic effect. The polypeptides themselves are also provided, as are methods of using such polypeptides and nucleic acids.

In one aspect, the disclosure features an isolated nucleic acid comprising the nucleotide sequence of SEQ ID NO:1. In some embodiments, the nucleic acid encodes a Kunitz-type inhibitor of Factor Xa (FXa).

In another aspect, the disclosure features a purified polypeptide containing the amino acid sequence of SEQ ID NO:2.

In some embodiments, the polypeptide possesses an activity selected from the group consisting of:
(i) decreasing FXa-mediated coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

In one aspect, the disclosure features a purified polypeptide consisting of the amino acid sequence of SEQ ID NO:2.

In another aspect, the disclosure features an isolated polypeptide that contains an amino acid sequence that is at least 70% (e.g., 75%, 80%, 82%, 85%, 86%, 87%, 88%, 89%, 90%, 91%, 92%, 93%, 94%, 95%, 96%, 97%, 98%, or 99%) identical to the amino acid sequence of SEQ ID NO:2, wherein the polypeptide possesses an activity selected from the group consisting of:
(i) decreasing FXa-mediated coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

In one embodiment, the polypeptide consists of an amino acid sequence that is at least 70% (e.g., 75%, 80%, 82%, 85%, 86%, 87%, 88%, 89%, 90%, 91%, 92%, 93%, 94%, 95%, 96%, 97%, 98%, or 99%) identical to the amino acid sequence of SEQ ID NO:2.

In one aspect, the disclosure features an isolated polypeptide that contains an amino acid sequence that differs from the amino acid sequence of SEQ ID NO:2 by up to twenty-five (e.g., by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five) amino acid substitutions, additions, or deletions, wherein the polypeptide possesses an activity selected from the group consisting of:
(i) decreasing FXa-mediated coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

In some embodiments, the amino acid sequence differs from the amino acid sequence of SEQ ID NO:2 by up to twenty-five (e.g., by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five) conservative amino acid substitutions.

In other embodiments, the polypeptide consists of an amino acid sequence that differs from the amino acid sequence of SEQ ID NO:2 by up to twenty-five (e.g., by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five) amino acid substitutions, additions, or deletions.

In some embodiments, the amino acid sequence differs from the amino acid sequence of SEQ ID NO:2 by up to twenty-five (e.g., by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five) conservative amino acid substitutions.

In another aspect, the disclosure features a purified polypeptide containing the amino acid sequence of SEQ ID NO:3.

In some embodiments, the polypeptide possesses an activity selected from the group consisting of:
(i) decreasing FXa-mediated coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

In another aspect, the disclosure features a purified polypeptide consisting of the amino acid sequence of SEQ ID NO:3.

In one aspect, the disclosure features an isolated polypeptide that contains an amino acid sequence that is at least 70% (e.g., 75%, 80%, 82%, 85%, 86%, 87%, 88%, 89%, 90%, 91%, 92%, 93%, 94%, 95%, 96%, 97%, 98%, or 99%) identical to the amino acid sequence of SEQ ID NO:3, wherein the polypeptide possesses an activity selected from the group consisting of:
 (i) decreasing FXa-mediated coagulation, wherein the decrease occurs in the presence of phospholipids;
 (ii) promoting apoptosis of B16F10 cells;
 (iii) promoting apoptosis of SKMEL28 cells;
 (iv) decreasing tumor mass in a C57BL/6J mouse implanted with B16F10 tumor cells;
 (v) decreasing tumor metastasis in a C57BL/6J mouse implanted with B16F10 tumor cells;
 (vi) decreasing angiogenesis in a C57BL/6J mouse implanted with B16F10 tumor cells; and
 (vii) increasing macrophage phagocytic activity in a C57BL/6J mouse implanted with B16F10 tumor cells.

In some embodiments, the polypeptide consists of an amino acid sequence that is at least 70% (e.g., 75%, 80%, 82%, 85%, 86%, 87%, 88%, 89%, 90%, 91%, 92%, 93%, 94%, 95%, 96%, 97%, 98%, or 99%) identical to the amino acid sequence of SEQ ID NO:3.

In another aspect, the disclosure features an isolated polypeptide that contains an amino acid sequence that differs from the amino acid sequence of SEQ ID NO:3 by up to twenty-five (e.g., by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five) amino acid substitutions, additions, or deletions, wherein the polypeptide possesses an activity selected from the group consisting of:
 (i) decreasing FXa-mediated coagulation, wherein the decrease occurs in the presence of phospholipids;
 (ii) promoting apoptosis of B16F10 cells;
 (iii) promoting apoptosis of SKMEL28 cells;
 (iv) decreasing tumor mass in a C57BL/6J mouse implanted with B16F10 tumor cells;
 (v) decreasing tumor metastasis in a C57BL/6J mouse implanted with B16F10 tumor cells;
 (vi) decreasing angiogenesis in a C57BL/6J mouse implanted with B16F10 tumor cells; and
 (vii) increasing macrophage phagocytic activity in a C57BL/6J mouse implanted with B16F10 tumor cells.

In some embodiments, the amino acid sequence differs from the amino acid sequence of SEQ ID NO:3 by up to twenty-five (e.g., by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five) conservative amino acid substitutions.

In other embodiments, the polypeptide consists of an amino acid sequence that differs from the amino acid sequence of SEQ ID NO:3 by up to twenty-five (e.g., by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five) amino acid substitutions, additions, or deletions.

In some embodiments, the amino acid sequence differs from the amino acid sequence of SEQ ID NO:3 by up to twenty-five (e.g., by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five) conservative amino acid substitutions.

In one aspect, the disclosure features a purified polypeptide containing amino acids 1-61 of SEQ ID NO:3.

In another aspect, the disclosure features a purified polypeptide containing amino acids 62-108 of SEQ ID NO:3.

In yet another aspect, the disclosure features a pharmaceutical composition containing a nucleic acid described herein (e.g., SEQ ID NO:1).

In another aspect, the disclosure features a pharmaceutical composition containing a polypeptide described herein (e.g., a polypeptide containing SEQ ID NO:2 or 3).

In one aspect, the disclosure features a method of decreasing blood coagulation in a subject, the method comprising administering a polypeptide described herein (e.g., a polypeptide containing SEQ ID NO:2 or 3) to the subject.

In another aspect, the disclosure features a method of treating cancer in a subject, the method comprising administering a polypeptide described herein (e.g., a polypeptide containing SEQ ID NO:2 or 3) to the subject. In some embodiments, the polypeptide is administered with a chemotherapy treatment. In some embodiments, the polypeptide is administered with a radiotherapy treatment.

In one aspect, the disclosure features a method of decreasing tumor progression in a subject, the method comprising administering a polypeptide described herein (e.g., a polypeptide containing SEQ ID NO:2 or 3) to the subject.

In one aspect, the disclosure features a method of decreasing tumor metastasis in a subject, the method comprising administering a polypeptide described herein (e.g., a polypeptide containing SEQ ID NO:2 or 3) to the subject.

In one aspect, the disclosure features a method of decreasing tumor angiogenesis in a subject, the method comprising administering a polypeptide described herein (e.g., a polypeptide containing SEQ ID NO:2 or 3) to the subject.

In one aspect, the disclosure features a method of increasing phagocytic activity in a subject, the method comprising administering a polypeptide described herein (e.g., a polypeptide containing SEQ ID NO:2 or 3) to the subject.

In one aspect, the disclosure features a method of treating or preventing a thromboembolism in a subject, the method comprising administering a polypeptide described herein (e.g., a polypeptide containing SEQ ID NO:2 or 3) to the subject.

In some embodiments, the method is performed in a pre or post operative setting.

In one aspect, the disclosure features a vector containing a nucleic acid described herein (e.g., SEQ ID NO:1).

In one aspect, the disclosure features a host cell that contains a vector described herein (e.g., a vector containing a nucleic acid described herein (e.g., SEQ ID NO:1)).

In another aspect, the disclosure features a method of producing a Kunitz-type inhibitor of Factor Xa (FXa), the method comprising culturing a host cell described herein (e.g., a host cell that contains a vector described herein) under conditions that result in the expression of the inhibitor encoded by the nucleic acid.

In some embodiments, the method further includes purifying the inhibitor from the host cells or host cell culture supernatant.

DESCRIPTION OF DRAWINGS

FIG. 4: Complete sequence of the selected clone (SEQ ID No.1).

FIG. 5: Translation of the sequence of nucleotides of the selected clone for the proteic sequence (SEQ ID No.2).

FIG. 6: Sequence of the mature protein (SEQ ID No.3).

FIG. 9: Comparison of the primary structures of the Amblyomin-X and of the Ixodes.

FIG. 10: Curve of FXa inhibition in presence of phospholipids and crescent concentrations of the recombinant inhibitor.

FIG. 11a: Prolonging curve of thromboplastin time partially activated in absence and presence of crescent concentrations of the recombinant inhibitor.

FIG. 11b: Inhibition curve of prothrombin time (TP) in absence (control) and crescent concentrations of the recombinant inhibitor.

FIG. 24: Macroscopic aspect of dorsal tumors of B16F10 melanoma treated during 42 days with Amblyomin-X.

FIG. 25 A: Macroscopic aspect of B16F10 dorsal melanoma in C57BL/6J mice of the control group treated during 42 days with saline solution.

FIG. 25 B: Macroscopic aspect of B16F10 dorsal melanoma tumor in C57BL/6J mice treated during 42 days with Amblyomin-X.

DETAILED DESCRIPTION

Figure 1:
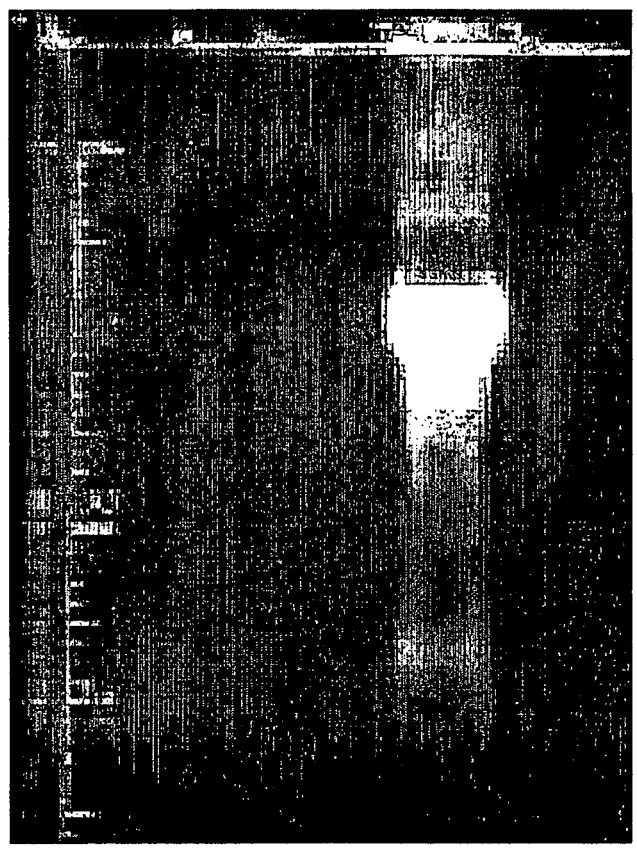
FIG. 1: Electrophoresis in agarose gel. Sample: total RNA extracted from the *A. cajennense* salivary glands by the guanidine phenyl isothiocyanate method.

This invention verifies and proves that a protein present in the saliva of the *Amblyomma cajennense* tick has apoptotic activity in tumoral cells (of human melanoma-SKMEL28, MEL85, MEWO, murine melanoma B16F10, leukemia: promyelocytic HL60, erythroleukemia K562, lymphoblastic T JURKAT, leukemia T U937, murine lymphocytic T, YAC-I; lung cancer H292, breast cancer MCF-7 and MCF-IO and rectum colon cancer SW613-12A1, SW613-B3), and antitumoral activity in vivo (melanoma), as well as antimetastatic and anti-angiogenic activity.

This invention also shows that the recombinant protein is able to stimulate the phagocytic activity of macrophages (spreading and phagocytary rates mediated by complement or antibody) and does not have cytotoxic activity in normal cells as human endothelial cells derived from umbilical cord, fibroblasts, platelets, polymorphonuclear, lymphocytes and human macrophages, as well as in internal organs as kidneys, liver, heart, spleen and lungs, in which no histopathologic alteration was observed after a prolonged treatment with the protein.

According to this invention a recombinant protein is obtained, a new Factor X activated inhibitor, a new anti-tumoral, anti-metastatic and anti-angiogenic agent, obtained from a gene of a cDNA library of the salivary glands of the *Amblyomma cajennense* tick.

What was obtained through this invention is composed of a sequence of amino acids determined from the cDNA of the *Amblyomma cajennense* gland and can be defined as a polypeptide or protein of which sequence was determined from the cDNA that codifies between bases 1 and 505.

Specifically, it is composed of a recombinant protein called Amblyomin-X and has a two-domain protein presenting homology to the Kunitz- and MAP Kinase-type domains.

This invention presents anti-cancer use action as well as enables vaccine development from the cDNA.

In general lines this invention is based initially on a cDNA library built up from salivary glands of the *Amblyomma cajennense* tick and subsequent sequencing of aleatory genes.

Among the sequences obtained, one was identified as having homology with serine protease inhibitors (SERPINS). The complete sequence of the elected gene was analyzed in a data bank and showed 17% of homology with the human TFPI of type 1 (Tissue Factor Pathway Inhibitor) and 21% of homology with the Ixolaris (*Ixodes scapularis* tick isolated inhibitor). The protein was expressed in *E. coli* bacteria in form of inclusion corpuscle and obtained after solubilization with urea and β-mercaptoethanol and later purified in affinity column of Ni-Sepharose.

The recombinant protein is a 13.5 kDa and is able to inhibit Factor X activated in purified systems only when in presence of phosphatidylcholine and phosphatidylserine phospholipids. Besides that, the recombinant protein is able to prolong plasma coagulation time, observed in global coagulation tests as TTPA and TP. The recombinant protein did not demonstrate effect on normal endothelial cells (HUVECs-Human Vein Endothelial Cells) or on normal human fibroblast lineages.

However, it produces cellular death by apoptosis in several lineages of tumoral cells; among them, the murine melanoma (B16F10).

Mice C57BI/6J with B16F10 melanotic melanoma were treated with the recombinant protein by intraperitoneal and subcutaneous route using different doses and in different time spacing. It was observed that the treated animals showed a significant reduction of tumoral mass (dorsal tumor). Besides that, the indices of metastasis were dramatically reduced when the treatment was conducted during 14 days after the tumoral implanting. When the treatment was conducted after the third day of the tumoral implanting, a complete remission of the tumor and the absence of metastases were observed. The protein seems to have anti-angiogenic activity since it inhibited vessel formation around the implanted tumor when compared to the control (without treatment).

The protein also demonstrated to activate the phagocytic activity of macrophages both in vitro and in vivo.

Complete hemograma of the control and treated animals were conducted and the preliminary results suggest that this protein inhibits the pro coagulant state present in animal with tumors. Besides that, the hematocrit and the hemoglobin levels are close or the same to those of healthy animals (without tumor) demonstrating that the protein not only protects the animal against anemia but also apparently does not alter bone marrow or cause haemorrhagic phenomena for its FXa inhibiting capacity and long time treatment.

Advantages compared to usual treatments:

It is indicated as a biologic agent instead of chemotherapy. Therefore it should act only in sick cells not in healthy ones avoiding the side effects of chemotherapy.

For its FXa inhibitory potential it could be used as a thromboembolism protector (anticoagulant) in patients submitted to chemotherapy treatment or in patients with prothrombotic characteristics.

As a recombinant it can be obtained in larger amounts.

The methodology applied in the obtainence process and in the analysis of the referred recombinant protein can be summarized by the following procedures: Feeding the ticks and extracting their salivary glands; Obtainence of the total RNA by the guanidine phenol isothiocyanate method; Quantification of RNA; Agarose gel electrophoresis for DNA; Agarose gel electrophoresis for RNA; Purification of mRNA in oligo affinity column (dT); Construction of a cDNA library; Synthesis of the first strand; Synthesis of the second strand; Size screening of cDNA fragments in agarose gel; cDNA binding to Eco RI Adaptors; Digestion with Not I; Size screening of cDNA in agarose gel; cDNA binding to the vector; Transformation of competent bacteria; Preparation of plasmidial DNA by the alkaline lysis method; Preparing samples for sequencing; Searching for sequences; Amplification of selected clone; Synthesis of the initiator oligonucleotide in PCR reaction; Polymerase Chain Reaction (PCR); Selection of the recombinant plasmids in agarose gel; Digestion of the plasmidial DNA with restriction enzymes; Binding to the expression vector; Induction of the expression in small scale; Expression of proteins; Structural Studies; Analysis of the secondary structure of the recombinant; Analysis of the primary structure and model of the tertiary structure; Biochemical Assays; Inhibition of FXa in presence of phospholipids; Coagulation Tests; Human and Murine Tumoral Lineage Culture; Treatment of Tumoral Cells with the Amblyomin-X Recombinant Protein; Determination of the DNA content by Flow Cytometry; Determination of the Cellular Cycle Phases by Flow Cytometry; Tumoral lineages cultures and Tumoral Implanting in Animals; Observing Tumoral Growing; Determining the Cytotoxic Activity; Obtainence of Peritoneal Macrophages; Culture of Human Skin Fibroblasts and Statistical Analysis.

For achieving this invention the following materials were preferably used:

lineage: *Escherichia coli;*

1) Strain DH5α: ø80 dlacZΔM15, recA1, endA1, gyrA9β, thi-1, hsdR17 ($r_k^-$, $m_k^+$), SupE44, relA1, deoR Δ(lac ZYA-arg I) ul69.

2) Strain BL21 (DE3): F', ampT, hsdS$_B$($r_8^-$, $m_8^-$), dcm, gal (DE3).

Bacteriophage DE3 contains the RNA polymerase gene of phage T7 under the control of promoter Lac UV5, inductive with isopropil-thio-β-galactoside (IPTG).

Plasmids:

1) pGEM-11Zf(+): vector digested with EcoR I and Not I used for building up the plasmidial library. Technical Manual of PROMEGA, 1999.

2) "easy" pGEM-T: the "easy" pGEM-T plasmid contains the T7 and SP6 promoters flanking the MCS ("multiple cloning site") for the sub-clonage of PCR products. Technical Manual PROMEGA, 1999.

3) pAE: expression vector derived from pRSETA (Invitrogen) and from pET3-His (Chen, 1994) constructed at the Laboratory of Molecular Biotechnology of Butantan Institute (Ramos et al, 2003).

pAE is a high expression vector that combines the efficiency of promoter T7 and a great number of pRSETA plasmid copies, with a N-terminus fusion of six non-removable histidines of pET3-His, that allows the purification of recombinant proteins by affinity chromatography with immobilized metal ("Immobilized Metal Affinity Chromatography", IMAC). The addition of this small fusion does not interfere in the activity of the majority of the studied recombinant proteins.

The process for the Synthesis of initiator oligonucleotides in the PCR reactions starts as follows:

The "sense" oligonucleotides (P1 and P2) were obtained based on the protein N-terminus sequence. To these oligonucleotides a restriction site was preferably added for subsequent unidirectional clonage. The "sense" and "anti-sense" oligonucleotides were also used. They were all diluted in TE buffer (Tris-HCl 10 mM, EDTA 1 mM) for a final concentration of 10 pmol/μl (100 μM).

In what concerns the preparation of mRNA the following procedures were conducted:

Domestic rabbits (*Oryctolagus cuniculus*) were infested with *Amblyomma cajennense* ticks and after feeding time, the female ticks were taken out and their saliva and salivary glands were collected using sterilized surgical materials. The salivary complexes of ticks were dissected, deposited in "cryo-tubes", immediately frozen in liquid Nitrogen and stored in freezer at −80° C.

Total RNA Extraction

The salivary glands were sunk in guanidine isothiocyanate phenol reagent according to the methodology recommended by the manufacturer manual.

Total RNA Eletrophoretic Profile

The accessories of the electrophoresis system were treated with hydrogen peroxide ($H_2O_2$) 3% for eliminating RNAase and were washed with water treated with DEPC autoclaved. Agarose gel 1.5% in sodium phosphate buffer 10 mM, pH 7.0, was deposited in the plate. Two samples containing 10 or 15 μl of total RNA (16.7 ng/μl), 5 μl of sample buffer and DEPC treated $H_2O$ for a final volume of 25 μl were applied in the gel. The migration of the samples was conducted in 5 V/cm until the bromophenol reaches ⅔ of the gel.

mRNA Purification in Oligo (dT) Cellulose Affinity Column mRNA was purified in oligo dT cellulose affinity column washed with NaOH 0.1 N and balanced with 1 ml of binding buffer Tris-HCl 10 mM, EDTA 1 mM, NaCl 300 mM, SDS 0.1%, pH 7.0.

3 ml of binding buffer was added to the total RNA followed by incubation at 70° C. for 5 minutes, cooling it in ice for another 5 minutes and applying it in affinity column. The column was drained by gravity and washed with more 4 ml of binding buffer for eliminating all the RNA that were not mRNA.

The mRNA was eluded with 1.5 ml of buffer Tris-HCl 10 mM, EDTA 1 mM, SDS 0.1%, pH 7.0 and collected in clean treated tube, heated at 70° C. for 5 minutes and cooled in ice for another 5 minutes. After incubation for 20 minutes at room temperature, 90 μl de NaCl 5 M was added to the material and it was applied again in the column rebalanced with binding buffer. After a new wash with 4 ml of binding buffer and eluded with 1.5 ml of the elution buffer the collected material was precipitated with 90 μl of NaCl 5 M and 3 ml of absolute ethylic alcohol at –80° C. "overnight". The material was then centrifuged in 7000 g for 20 minutes at 4° C. and the supernatant was eliminated.

mRNA was washed with 1 ml of ethylic alcohol 75% and centrifuged in 7000 g for 2 minutes at 4° C. After drying it the mRNA precipitated was re-suspended in 20 μl of DEPC treated $H_2O$ and stored at –80° C.

mRNA Quantification

For a 500-μl final volume 2 μl of mRNA were added in 498 μl of $H_2O$ milli-Q autoclaved. The optical density readings were conducted in 260 and 280 nm in quartz cuvets of 500 μl. The mRNA concentration was calculated based on the following equation:

$$[RNA] = A_{260} \times D \times 40 \text{ μg/ml}$$

Where, D=dilution factor. In what concerns the build up of the cDNA library, the following procedures were taken:

The cDNA library was built up based on 5.0 μg of isolated mRNA using preferably the Superscript™ Plasmid System for cDNA Synthesis and Plasmid Cloning (Life Technologies) kit modified.

First Strand Synthesis 5.0 μg of mRNA were diluted in 6 μl of DEPC treated $H_2O$ in which 1.5 μl of NotI adaptor primer was added and heated at 70° C. for 10 minutes, cooled in ice bath and rapidly centrifuged. 4 μl of first strand buffer 5×, 2 μl of DTT 0.1 M, 1 μl of dNTP 10 mM mixture and 0.5 μl of $H_2O$ were added to the tube. The reaction was homogenized, rapidly centrifuged and balanced at 44° C. for 2 minutes. 5 μl of the Super Script II RT enzyme was added and the mixture was incubated at 44° C. for more 90 minutes. Cooling process at 4° C. interrupted the reaction.

Second Strand Synthesis

91 μl of $H_2O$, 30 μl of second strand buffer, 3 μl of dNTP 10 mM mixture, 1 μl of *E. coli* DNA ligase 10 U/μl, 4 μl of *E. coli* DNA polymerize I 10 U/ml and 1 μl of *E coli* RNAase H (2 U/μl) were added to the first strand reaction mixture. After gently stirring the mixture, it was incubated at 16° C. for 2 hours and 2 μl of T4 DNA polymerize I was added with more 5 minutes of incubation at the same temperature. Cooling in ice and adding 10 μl of EDTA 0.5 M interrupted the reaction.

Screening of Fragment Sizes in Agarose Gel

The complete second strand reaction added with 17 μl of Ficoll free of xylene cyanol was applied in agarose gel 1% and after 1 cm of sample migration in 80 V of electrophoresis system two bands were cut out of the gel; one containing fragments between 400 and 800 pb (low weight stored in freezer at –80° C.) and the other with fragments over 1000 pb (of high weight, used for continuing this invention).

DNA was purified from the gel using preferably the Concert Gel Extraction Systems (Life Technologies) kit and the cDNA eluded with 50 μl of $H_2O$ heated at 65° C. and concentrated into 30 μl in a vacuum concentrator device.

cDNA Binding to the EcoR I Adaptors

10 μl of buffer T4 DNA ligase 5×, 5 μl of Eco RI adaptors and 5 μl of T4 DNA ligase with posterior incubation at 16° C. for 16 hours were added to the reaction tube. After that, the reaction was heated at 65° C. for 10 minutes and cooled in ice. After adding 2 μl of ATP solution and 2 μl of T4 polymerase kinase the reaction was incubated for 30 minutes at 37° C.

The cDNA was extracted with 55 μl of phenol/chloroform/isoamilic alcohol (25:24:1), stirred and centrifuged in 14000 g for 5 minutes at room temperature. The upper aqueous phase was transferred to another tube and added with 2 volumes of absolute ethanol and 1 volume of sodium acetate 3 M and cooled at –80° C. for 1 hour. After centrifuging it in 14000 g for 20 minutes and washing it with 500 μl of ethanol 70%, cDNA was dried up in flow for about 5 minutes.

Digestion with NotI

41 μl of $H_2O$, 5 μl of specific reaction buffer, 4 μl of NotI were added to the precipitated gently homogenizing it and submitted to incubation for 2 hours at 37° C.

Second Size Screening in Agarose Gel

50 μl of the reaction of high molecular weight fragment was applied in agarose gel 1% and after electrophoresis the bands were cut out of the gel and the high weight cDNA was purified and eluded with 50 μl of $H_2O$ as described in the first size screening (Screening of fragment sizes in agarose gel).

cDNA Unidirectional Binding to the pGEM11Zf (+) Vector

The high weight fraction (14 μl) was added with 4 μl of T4 DNA ligase buffer, 1 μl of clonage vector, preferably pGEM11Zf (+) (previously digested with EcoR I-Not I enzymes) and 1 μl of T4 DNA ligase and incubated at 16° C. for 18 hours.

The process of bacterial transformation of this invention follows the procedures described bellow:

Transformation of Competent *E. coli* DH5α

High weight DNA (2 μl) was added to 50 μl of calcium competent bacteria (DH5α) stored at –80° C. and previously defrosted in ice for 15 minutes. The solutions were incubated for 30 minutes in ice and submitted right after to a thermal chock at 42° C. for 2 minutes and again to ice for 5 minutes.

350 μl of SOC medium was added to the transformed bacteria and transferred to aerated tubes and incubated at 37° C. under stirring condition (220 rpm/min) for 90 minutes. The cDNA was plated (2001 of high molecular weight cDNA) with 2YT-ampicillin medium and the plates were incubated for 18 hours at 37° C. 20 colonies containing inserts were incubated in two plates at 37° C. in 2.5 ml of 2YT-ampicilina 100 µg/ml medium for 18 hours under stirring of 200 rpm. The cDNAs were purified using preferably the mini-prep-Concert Rapid Plasmid (Life Technologies) kit eluded with 50 µl of TE at 65° C.

For the analysis of the plasmid library, the following procedures were taken:

Plasmids (4 µl) were digested at 37° C. for 2 hours in presence of 1 µl of specific reaction buffer, 4 µl of water, 0.5 µl of EcoRI (10 U/µl) enzyme. The 0.51 µl of HindIII (10 U/µl) and the fragments generated were analyzed in agarose gel 1% with ethidium bromide. All the analyzed plasmids were submitted to sequencing.

Aiming to obtain the library amplification, mixtures containing 50 µl of calcium-competent bacteria DH5α and 5 µl of high molecular weight DNA bound to the clonage vector, were incubated 30 min in ice for 2 min at 42° C. and again in ice for more 5 min. After this, 10 ml of 2YT/ampicillin 100 µg/ml medium was added. The solutions were gently homogenized and aliquots of 2.5 ml were transferred by pipettes into deaerated tubes and incubated at 37° C. for 18 h. The plasmidial DNA was extracted using mini-prep columns, eluded with 50 µl of $H_2O$ at 65° C. and stored at −20° C.

Polymerize Chain Reaction (PCR)

The PCR "Polymerase Chain Reaction" reactions prepared for a final volume of 50 µl contained 1 µl of dNTPs 10 mM, 5 µl of Buffer for Taq DNA Polymerize 10×, 1.5 µl of MgSO4 50 mM, 0.5 µl of TaqDNA polymerize 2.5 U. For amplifying the cDNA that codifies for the inhibitor, 4 µl of the plasmidial DNA amplified, 4 µl of the oligonucleotide P1 10 pM and 2 µl of the oligonucleotide SP6 10 pM were used. The reaction was incubated in a thermocycler in which a program of initial denaturation at 94° C. for 3 min, 30 cycles of denaturation (94° C. for 45 seconds), annealing (50° C. for 25 seconds), extension (72° C. for 4 min) and a final extension at 72° C. for 15 min was conducted. After that, the samples were applied in agarose gel 1%. After 2 h of eletrophoretic migration in 80 V, the bands correspondent to the expected amplification products were cut out of the gel and the DNA was extracted and eluded in 30 µl of $H_2O$ for binding to a second clonage vector, preferably the "pGEM-T Easy Vector Systems" (Promega).

For proceeding the DNA binding to the plasmid the following methodology was performed:

The bindings were conducted for a final volume of 10 µl containing 6 µl of the PCR product (1700 pb), 1 µl of pGEM-T vector, 2 µl of buffer T4 DNA ligase 5× and 1 µl of T4 DNA Ligase 1 U/µl at 16° C. for 18 hours.

Strains of *E. coli* DH5α were incubated with 5 µl of binding reaction vector-insert and plated. Out of the formed colonies, 20 were collected for pre-inoculum and "mini-prep", exactly according to the protocol described for the transformation of DH5α competent *E. coli*.

Selection of Recombinant Plasmids in Agarose Gel

Before processing the "mini-preps" reactions, 300 µl of each pre inoculum was submitted to a rapid phenol: chloroform purification process. After that, 20 µl of each sample were applied in agarose gel 1%, in TAE IX buffer. After the electrophoretic running, the gel was stained with 0.1 µg/ml of ethidium bromide solution for selecting the larger recombinant plasmids exposed to UV light. The positive clones of the item mentioned before were submitted to the mini-preps and eluted with 60 µl of water.

Digestion of the Plasmidial DNA with Restriction Enzymes

The DNAs of the purified clones amplified by PCR using both P1 and P2 primers, were digested at 37° C. for 2 h in a solution containing 5 µl of plasmidial DNA, 2 µl of specific reaction buffer, 0.5 µl of EcoRI (10 U/µl), 0.5 of Xho I (10 U/µl) and 12 µl of $H_2O$ for a final volume of 20 µl.

The same plasmidial DNAs (5 µl) were incubated in same conditions with 1 µl of specific reaction buffer 1 µl of EcoR I (10 U/µl) and 12 µl of water.

The digestion products were analyzed in agarose gel 1%. The library clones and the DNAs subcloned in "easy" pGEM-T were sequenced.

For executing the DNAs sequencing the method of chain termination by dideoxynucleotide was conducted adapting it for the automatic sequencer. 400 ng of plasmidial DNA were prepared through the purification by mini-preps that were used as mold in the sequencing reaction. The described oligonucleotides, T7 and SPB were used in the reactions. After the thermocycling, the amplification products were separated in DNA sequencing gel of 36 cm of length (4.25% acrylamide:bis-acrylamide in proportion of 19:1, in 1×TBE and 7 M Urea). The detecting system of this device is composed of a laser source and a fluorescence detector placed at the lower part of the sequencing gel. Each dNTP emits a specific fluorescence captured by the detector and it sends the information to a computer that automatically registers the nucleotide position in the electropherogram. The running was conducted for 7 hours. All the sequenced DNAs were compared with the "GenBank" sequences based on the algorithm for BLASTx and BLASTn programs or FASTA program.

The expression process of the recombinant protein preferably in the BL21 (DES) strain of *E. coli* applied in this invention follows the procedures described below:

Binding to the pAE Vector

The positive clones in which the sequenced inserts confirmed the Amblyomin-X sequence were incubated in 7 ml of LB/ampicillin at 37° C. for 18 hours, and were then submitted to mini-preps and eluted with 50 µl of water.

The purified DNAs were digested at 37° C. for 5 h in a solution containing 20 µl of plasmidial DNA, 5 µl of specific reaction buffer, 1.0 µl of EcoR I (10 U/µl), 1.0 µl of Xho I (10 U/µl) and 23 µl of $H_2O$ for a final volume of 50 µl.

After preparative electrophoresis in agarose gel 1%, the bands with around 1000 pb were purified from the gel and eluded with 30 µl of $H_2O$ and dried in vacuum at 45° C. for 1 h.

The plasmid was re-suspended in 10 µl of $H_2O$ and 3.5 µl of it was incubated at 16° C. for 18 h with 3.5 µl of the pAE expression vector (FIG. 4), 2 µl of buffer 5× for DNA ligase and 1 µl of DNA ligase. The clones subcloned in pAE vector were also sequenced.

Induction of the Amblyomin-X Expression

Aiming to obtain great quantities of the soluble recombinant protein the BL21 (DE3) strain of the *E. coli* bacteria was preferably used for the expression of this protein since it is a strain presenting fast growing, easy culture and maintenance and high quantity of recombinant protein. This strain of *E. coli* is lysogenic and does not have post-translation modification systems.

Cultures of *E. coli* transformed preferably with the recombinant expression vector (pAE-clone 14.16) (FIG. 4) were inoculated in 3 ml of LB/ampicillin (100 µg/µl) medium and incubated at 37° C. until the obtainence of a $DO_{600\,nm}$ of 0.5. For the non induced control 1 ml of the pre-inoculum was stored at 4° C. IPTG for 0.5 mM was added to the rest of the volume and incubation was maintained for more 3 h. 10 µl of application buffer SDS-PAGE with β-mercaptoethanol 0.1 M was added to each 40 µl of culture. The samples were boiled for 12 min and applied in polyacrilamide gel 12.5%. Afterwards, the gel was stained with 0.25% of "Coomassie Blue Brillant" in 50% methanol for 18 h and destained with acetic acid 10% in water for 3 h at room temperature.

For obtaining the protein expression (Lopap) of this invention, the following procedures were taken:

Cultures of *E. coli* transformed with the expression vector were inoculated in 100 ml of LB/ampicillin (100 μg/μl) medium and incubated at 37° C. until obtaining a $DO_{600\,nm}$ of 0.5. Aliquots of 25 ml were incubated in 4 different bottles with 500 ml of LB/ampicillin (100 μg/μl) for 90 min. at 37° C. IPTG was then added for the final concentration of 1 mM and the incubation was maintained for more 4 h. The medium was then centrifuged in 12000 rpm and frozen at −70° C. for 18 h. The cells of the 4 bottles were then re-suspended in 70 ml of lysis buffer $NaH_2PO_4$ 50 mM, NaCl 300 mM, imidazol 10 mM and submitted to a French press in 2000 GAGE for three times and centrifuged in 5000 rpm for 15 min. at 4° C.

The supernatant that had the soluble expressed protein was centrifuged in 15000 rpm for 30 min for clarification and applied in affinity column of Ni-sepharose previously balanced with lysis buffer. The column was washed with buffer imidazol 80 mM, β-mercaptoethanol 5 mM, NaCl 500 mM, Tris HCl 50 mM pH 6.8 and the washing volume was collected. The protein was eluded using Tris-HCl 50 mM pH 8.0, imidazol IM, NaCl 100 mM with flow of Iml/5 min.

The "pellet" (corpuscles) of the medium submitted to the French press and centrifuged was re-suspended in 20 ml of buffer Tris-HCl 50 mM, Urea 1 M, Triton X-100 1%, pH 8.0 for eliminating hydrophobic components and centrifuged in 5000 rpm for 15 min at 4° C. The separated precipitated was incubated at room temperature overnight with 10 ml of buffer Tris-HCl 50 mM, NaCl 500 mM, Urea 8 M, β-mercaptoethanol 10 mM pH 8.0 for the solubilization of the corpuscles.

This material was again centrifuged in 4000 rpm for 20 min at 4° C. and the supernatant was added drop by drop to the "refolding" buffer Tris-HCl 50 mM, NaCl 500 mM, Imidazol 5 mM and β-mercaptoethanol 5 mM pH 8.0 (as an alternative for obtaining the protein with correct structure. Another approach for reaching this phase was to use the buffer added with $CaCl_2$ 100 mM) with constant stirring at room temperature for 18 h. The material was filtrated and applied in a Ni-sepharose column previously balanced with lysis buffer. The column was washed with 180 ml of buffer Tris-HCl 50 mM, NaCl 500 mM, Imidazol 20 mM pH 6.8 and eluded with Tris-HCl 50 mM pH 8.0, imidazol IM, NaCl 100 mM with flow of 1 ml/5 min.

The recombinant protein obtained was tested concerning its inhibitory capacity on Factor Xa, coagulation tests and control of tumoral cells.

The deposit of the sequence was included in data banks with access restriction up to April 2005 BANKIT 608848.

The biochemical assays for determining the inhibition of FXa were conducted in presence of phospholipids. The phospholipid membranes were prepared as described by Barenholz et al., 1977.

The FXa inhibition in presence of the phospholipid membrane was determined by the measure of the residual enzymatic activity on the amino-methyl-coumarin substrate with the hydrolysis site for FXa, or commercial chromogenic substrate.

The hydrolysis reactions conducted at 37° C. in buffer Tris/HCl 50 mM, pH 7.5-8.0 were monitored by the fluorescence in 380 nm (excitation) and 460 nm (emission) wave lengths by a spectrofluorimeter or spectrophotometer in 405 nm wave length in case of chromogenic substrates.

The recombinant protein of this invention when used in 5-10 uM doses, inhibits the amidolytic activity of human Factor X activated, in purified conditions, in presence of phosphatidylserine/phosphatidylcholine and in the plasma.

In doses from 0.3 to 1.2 uM, the protein induces apoptosis (programmed cellular death) in tumoral lineage cells (B16F10, SKMEL28) with cellular cycle stop in G2/M.

In these concentrations the protein does not induce apoptotic effects in normal cells (HUVECs, leukocytes polymorphonuclear, human fibroblasts, platelets and macrophages).

The treatment of C57BL/6J isogenic mice implanted with B16F10 melanotic tumor (with tumoral volume of approximately 0.5 $mm^3$ at the $12^{th}$. day) with 1.0 mg/Kg dose by intradermic route for 14 days showed that the Amblyomin-X recombinant protein is able to reduce significantly the tumoral mass and volume. It can also reduce the number of pulmonary, hepatic and spleenic metastases.

The treatment with the Amblyomin-X recombinant protein in a 0.5 mg/Kg dose administrated by intraperitoneal route during 42 days and initiated after the $3^{rd}$ day of implanting the B16F10 tumoral cells by endovenous route in C57BL/6J mice. The Amblyomin-X is able to cause complete remission of the tumoral mass and volume and impede significantly the formation of metastases. Anatomopathologic analysis of tumors and metastatic lesions in the lungs, liver and spleen of animals with tumor treated with Amblyomin-X and the comparison to those of non-treated animals, showed that the recombinant protein promoted a selective recognition of the tumoral cells inhibiting the proliferative capacity of the signal pathways of the MAP Kinase system and the neoangiogenesis leading to the cellular death. The microscopic analysis of the parenchyma of internal organs as liver, spleen and lungs did not present significant cytological alterations even after 42 treatment doses.

Hematological analysis of the animals with tumor submitted to the treatment showed that the recombinant protein improves significantly the hematological condition, maintaining the hematocrit, hemoglobin and cellularity within normality levels when compared to the non-treated ones with severe anemia.

According to this invention, a composting is obtained containing a sequence from the cDNA of the *Amblyomma cajennense* gland. This compost is composed of a polypeptide or protein which sequence was determined from the cDNA that codifies from base 1 to base 505.

The recombinant protein obtained from the compost was named Amblyomin-X. It is a protein of two domains, of Kunitz- and MAP Kinase-types, and it is useful in tumor treatments as well as for developing vaccines from cDNA. It does also present biologic activity for Factor Xa, X, and VII proteins and also in the Factor VIIa/TF complex, showing to be a potential candidate for the modulation of anticoagulant function.

The administration of the peptide, polypeptide or protein improves conditions of patients with diseases related to cardiovascular and thromboembolic complications; decreases metastases of malign tumors; decreases malign tumors growing and dissemination; inhibits metastases of malign tumors; anti-coagulant performance in pre and post surgery conditions it can be used for preventing thromboembolism in conditions that generate apoptotic bodies (molecules rich in phospholipids), in degenerative diseases and malign tumors it can be used for improving the immune response. It can be used as a co-treatment in chemotherapy treatment of malign tumors; as a co-treatment in radiotherapy treatment of malign tumors; as a co-treatment in chemotherapy treatment of malign tumors with thromboembolic complications. It can also be used as a co-treatment in radiotherapy treatment of malign tumors with thromboembolic complications; can modulate the programmed cellular death (apoptosis); can modulate the formation of new blood vessels in the tumor and can be used as an agent for target therapy.

Modeling the Amblyomin-X Tertiary Structure

From the sequence obtained by cDNA, a study approach was conducted for modeling the Amblyomin-X using the Swiss PDB Viewer 3.7 (b2) program and the Swiss Model Server. This invention has its applicability field toward medical and veterinarian sectors.

Polypeptides of the Invention

The present disclosure provides for polypeptides that contain a Kunitz-type domain and/or a MAP kinase-type domain. The polypeptides can have an anti-coagulation effect, e.g., by inhibiting FXa-mediated coagulation. The polypeptides can also have, for example, anti-cancer, pro-apoptotic, anti-metastatic, anti-angiogenic, and/or pro-phagocytic effects.

Exemplary polypeptides include polypeptides that contain, consist essentially of, or consist of a polypeptide of SEQ ID NO:2 or SEQ ID NO:3. A particularly preferred polypeptide contains, consists essentially of, or consists of the amino acid sequence of SEQ ID NO:3.

Also included are polypeptides that include an amino acid sequence at least about 70%, at least about 75%, at least about 80%, at least about 82%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identical or completely identical to a polypeptide containing, consisting essentially of, or consisting of SEQ ID NO:2, and polypeptides encoded by a nucleic acid that hybridizes under high stringency conditions to a nucleic acid that encodes the polypeptide of SEQ ID NO:2.

Also included are polypeptides that include an amino acid sequence at least about 70%, at least about 75%, at least about 80%, at least about 82%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identical or completely identical to a polypeptide containing, consisting essentially of, or consisting of SEQ ID NO:3 and, polypeptides encoded by a nucleic acid that hybridizes under high stringency conditions to a nucleic acid that encodes the polypeptide of SEQ ID NO:3.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences. Alignments of related proteins described herein are instructive for identifying amino acid positions that tolerate modification, e.g., insertion, deletion, and substitution, e.g., conservative or non-conservative substitution.

As used herein, the term "hybridizes under high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions.

Also included are polypeptides that contain, consist essentially of, or consist of an amino acid sequence that differs from the sequence of SEQ ID NO:2 by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five amino acid substitutions, additions, or deletions. They can be at any position, e.g., internal or terminal (e.g., at the N or C terminus).

Also included are polypeptides that contain, consist essentially of, or consist of an amino acid sequence that differs from the sequence of SEQ ID NO:2 by at least one, but not more than two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five amino acid substitutions, additions, or deletions. They can be at any position, e.g., internal or terminal (e.g., at the N or C terminus).

The disclosure also includes polypeptides contain, consist essentially of, or consist of an amino acid sequence that differs from the sequence of SEQ ID NO:2 by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five conservative amino acid substitutions. They can be at any position, e.g., internal or terminal (e.g., at the N or C terminus).

Also included are polypeptides that contain, consist essentially of, or consist of an amino acid sequence that differs from the sequence of SEQ ID NO:3 by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five amino acid substitutions, additions, or deletions. They can be at any position, e.g., internal or terminal (e.g., at the N or C terminus).

Also included are polypeptides that contain, consist essentially of, or consist of an amino acid sequence that differs from the sequence of SEQ ID NO:3 by at least one, but not more than two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five amino acid substitutions, additions, or deletions. They can be at any position, e.g., internal or terminal (e.g., at the N or C terminus).

The disclosure also includes polypeptides contain, consist essentially of, or consist of an amino acid sequence that differs from the sequence of SEQ ID NO:3 by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five conservative amino acid substitutions. They can be at any position, e.g., internal or terminal (e.g., at the N or C terminus).

As used herein, the term "conservative amino acid substitution" describes the substitution of one amino acid for another with similar characteristics, e.g. substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. The following substitutions are further non-limiting examples of conservative substitutions:

Alanine: replace with: D-Ala, Gly, Beta-Ala, L-Cys, D-Cys;

Arginine: replace with: D-Arg, Lys, D-Lys, homo-Arg, D-homo-Arg, Met, Ile, D-Met, D-Ile, Orn, D-Orn;

Asparagine: replace with: D-Asn, Asp, D-Asp, Glu, D-Glu, Gln, D-Gln;

Aspartic Acid: replace with: D-Asp, D-Asn, Asn, Glu, D-Glu, Gln, D-Gln;

Cysteine: replace with: D-Cys, S-Me-Cys, Met, D-Met, Thr, D-Thr;

Glutamine: replace with: D-Gln, Asn, D-Asn, Glu, D-Glu, Asp, D-Asp;

Glutamic Acid: replace with: D-Glu, D-Asp, Asp, Asn, D-Asn, Gln, D-Gln;

Glycine: replace with: Ala, D-Ala, Pro, D-Pro, -Ala, Acp;

Isoleucine: replace with: D-Ile, Val, D-Val, Leu, D-Leu, Met, D-Met;

Leucine: replace with: D-Leu, Val, D-Val, Leu, D-Leu, Met, D-Met;

Lysine: replace with: D-Lys, Arg, D-Arg, Homo-arg, D-homo-Arg, Met, D-Met, Ile, D-Ile, Orn, D-Orn;

Methionine: replace with: D-Met, S-Me-Cys, Ile, D-Ile, Leu, D-Leu, Val, D-Val;

Phenylalanine: replace with: D-Phe, Tyr, D-Thr, L-Dopa, His, D-His, Trp, D-Trp, Trans-3, 4 or 5-phenylproline, cis-3, 4, or 5-phenylproline;

Proline: replace with: D-Pro, L-I-thoazolidine-4-carboxylic acid, D- or L-1-oxazolidine-4-carboxylic acid;

Serine: replace with: D-Ser, Thr, D-Thr, allo-Thr, Met, D-Met, Met(O), D-Met(O), L-Cys, D-Cys;

Threonine: replace with: D-Thr, Ser, D-Ser, allo-Thr, Met, D-Met, Met(O), D-Met(O), Val, D-Val;

Tyrosine: replace with: D-Tyr, Phe, D-Phe, L-Dopa, H is, D-His;

Valine: replace with: D-Val, Leu, D-Leu, Ile, D-Ile, Met, D-Met.

The suitability of a variant (e.g., that carries one or more of amino acid substitutions, additions, or deletions) of a polypeptide sequence provided herein for use in a method described herein can be tested using a technique described herein. For example, one can test a candidate polypeptide (e.g., a peptide that differs from the polypeptide of SEQ ID NO:3 by an amino acid deletion, substitution, or addition) for its suitability in the methods of described herein. The suitability of the candidate polypeptide can be measured, e.g., in an assay measuring coagulation time, e.g., in the presence of phospholipids. The effects of the candidate polypeptide can be compared with one or more standards. For example, a suitable standard would be a polypeptide described herein, e.g., a peptide consisting of the amino acid sequence of SEQ ID NO:3. The effects of the candidate polypeptide and the polypeptide of SEQ ID NO:3, wherein both polypeptides are used at the same concentration, are compared. Suitability can be shown by the candidate causing a better or as good of an effect as the standard. Alternatively or in addition, suitability can be shown by the candidate causing an effect that is stronger than the effect caused by the standard.

One or more of the amino acids of SEQ ID NO:2 and SEQ ID NO:3, or another polypeptide described herein, can be D- or L-amino acids. The amino acids can be naturally occurring or non-naturally occurring (e.g., synthetic) analogs. The amino acids can be modified. Modifications include: acetylation (e.g., at the N-terminus of the peptide); alkylation (e.g., methylation); biotinylation; acylation; biotinylation; glutamylation; glycosylation (e.g., N- or O-glycosylation); isoprenylation (e.g., addition of farnesol and geranylgeraniol); lipoylation; phosphopantetheinylation; phosphorylation; sulfation; selenation; amidation (e.g., C-terminal amidation); ubiquitination; citrullination/deimination; deamidation; proteolytic cleavage; formylation; myristoylation; pyroglutamate addition; carbamylation; glycosyl phosphatidylinositol (GPI) addition; O-methylation; glypiation; sumoylation; acylation; hydroxylation; desmosine addition; deamination; oxidation (e.g., to aldehyde); imine formation; glycation; carbamylation; disulfide bond formation (e.g., creation of intra- or inter-molecular disulfide bridges); prenylation; palmitoylation; porphyrin ring linkage; flavin linkage; GFP prosthetic group (Thr-Tyr-Gly sequence) formation; lysine tyrosine quinone (LTQ) formation; topaquinone (TPQ) formation; succinimide formation; transglutamination; carboxylation; polyglutamylation; polyglycylation.

The N- and/or C-terminus of the polypeptide can be modified to increase stability, e.g., to decrease degradation, e.g., proteolytic degradation.

The polypeptide can be fused to a peptide, e.g., a peptide which alters half-life, e.g., a portion of serum albumin or a portion of an Ig molecule, e.g., the IgG constant region. In other embodiments, the polypeptide is associated with, e.g., covalently bound to, a non-peptide polymer, e.g., PEG, or other polymer which affects half-life. The polypeptide can be modified (e.g., the fragment can have N or C terminal modifications) to alter its properties, e.g., to make it more resistant to degradation.

The polypeptides can be modified to contain an epitope tag (e.g., a His (e.g., 6×His or poly-His), Myc, HA, GST, MBP, VSV, Thioredoxin, Beta-Gal, FLAG, or GFP tag, etc.) for example, to aid in the identification or purification of the polypeptide. Such a tag can be present, for example, on the N- or C-terminus of the polypeptide. A cleavage site (e.g., a recognition site for enterokinase, thrombin, TEV protease, PRESCISSION™ protease, intein 1 or intein 2, or a signal peptidase, etc.) can optionally be situated between the tag and polypeptide sequence so that the tag can be cleaved from the polypeptide. Such techniques are known in the art. See also *Current Protocols in Molecular Biology*, John Wiley and Sons, Inc, New York, N.Y.

The disclosure also includes a fragment of the polypeptide of SEQ ID NO:3 capable of binding to Factor Xa. In a preferred embodiment, the fragment is capable of inhibiting Factor Xa, e.g., the fragment is capable of inhibiting with at least 10, 30, 50, 70, or 90% of the specific activity of the full-length polypeptide. In a preferred embodiment, the fragment is at least 30, 40, 50, 60, 70, 80, 90, or 100 amino acids in length. The fragment can be fused to another peptide, e.g., a peptide which alters half-life, e.g., a portion of serum albumin or a portion of an Ig molecule, e.g., the IgG constant region. In other embodiments, the fragment is associated with, e.g., covalently bound to, a non-peptide polymer, e.g., PEG, or other polymer which affects half-life. In other embodiments, the fragment differs from the corresponding portion of SEQ ID NO:3 by 1, 2, 5, 10, or 15 or fewer amino acid residues. The fragment can be modified (e.g., the fragment can have N or C terminal modifications) to alter its properties, e.g., to make it more resistant to degradation. The fragment can, for example, have homology to (e.g., at least about 70%, at least about 75%, at least about 80%, at least about 82%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identity) or contain all or a portion of amino acids 1-61 of SEQ ID NO:3.

The disclosure also includes a fragment of the polypeptide of SEQ ID NO:3 having at least one biological activity of a MAP kinase. In a preferred embodiment, the fragment is at least 30, 40, 50, 60, 70, 80, 90, or 100 amino acids in length. The fragment can be fused to another peptide, e.g., a peptide which alters half-life, e.g., a portion of serum albumin or a portion of an Ig molecule, e.g., the IgG constant region. In other embodiments, the fragment is associated with, e.g., covalently bound to, a non-peptide polymer, e.g., PEG, or other polymer which affects half-life. In other embodiments, the fragment differs from the corresponding portion of SEQ ID NO:3 by 1, 2, 5, 10, or 15 or fewer amino acid residues. The fragment can be modified (e.g., the fragment can have N or C terminal modifications) to alter its properties, e.g., to make it more resistant to degradation. The fragment can, for example, have homology to (e.g., at least about 70%, at least about 75%, at least about 80%, at least about 82%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identity) or contain all or a portion of amino acids 62-108 of SEQ ID NO:3.

Nucleic Acids of the Invention

The present disclosure provides for nucleic acids that encode polypeptides that contain a Kunitz-type domain and/or a MAP kinase-type domain.

Exemplary nucleic acids include nucleic acids that contain, consist essentially of, or consist of the nucleotide sequence of SEQ ID NO:1.

Also included are nucleic acids including nucleic acids that are at least about 70%, at least about 75%, at least about 80%, at least about 82%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identical or completely identical to a nucleic acid containing, consisting essentially of, or consisting of SEQ ID NO:1, and nucleic acids that hybridize under high stringency conditions to the complement of SEQ ID NO:1. Such nucleic acids can encode a polypeptide (e.g., a polypeptide described herein) that has an activity described herein, e.g., an anti-coagulation (e.g., by inhibiting FXa-mediated coagulation), anti-cancer, pro-apoptotic, anti-metastatic, anti-angiogenic, and/or pro-phagocytic effect.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences. Alignments of related proteins described herein are instructive for identifying amino acid positions that tolerate modification, e.g., insertion, deletion, and substitution, e.g., conservative or non-conservative substitution.

As used herein, the term "hybridizes under high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions.

EXAMPLES

Example 1 mRNA Obtainence

The total RNA integrity extracted from the salivary glands of the *A. cajennese* tick was verified in agarose gel in presence of formaldehyde (FIG. 1).

Example 2 mRNA Isolation

Figure 2:
FIG. 2: Electrophoresis in agarose gel. 1. and 2. mRNA purified by oligo (dT) column; 3. Material not retained in the oligo (dT) column; 4. Total RNA.

For the isolation of the mRNA, 48 ul of total RNA was diluted in 500 ul of 10 mM Tris buffer in presence of 1mM EDTA and submitted to the oligo (dT) cellulose affinity column. 17.28 ug of mRNA was obtained. The ratio $A_{260/280}$ for the mRNA was 1.71 (ug/ul). The extracted mRNA, free of degradation products, was used for the construction of the cDNA library (FIG. 2).

Example 3

The Construction of the cDNA Library

By selection in agarose gel from the cDNA library with inserts larger than 800 pb.

Figure 3:
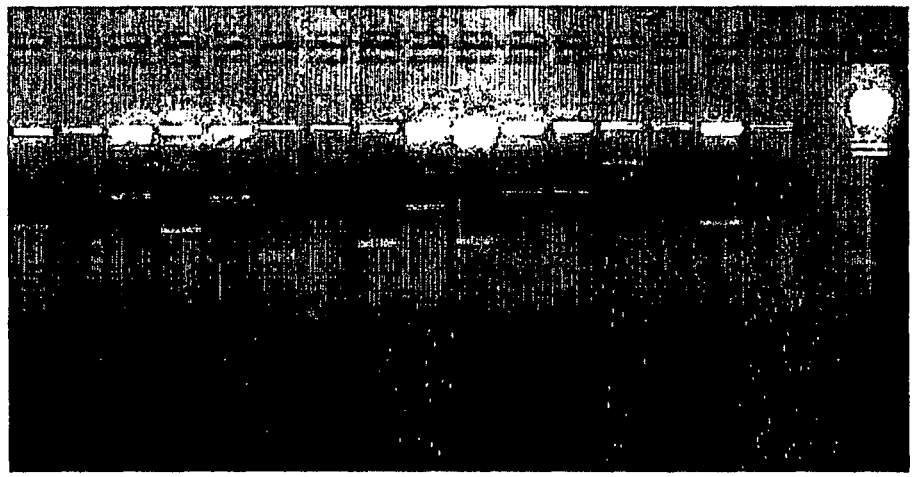
FIG. 3: cDNA inserts of the plasmid library. Electrophoresis in agarose gel 1-2% showing the fragments obtained by 16 aleatory clones of the plasmid library after the incubation for 2 hours with EcoR I and Hind III From 1 to 16: cleavage products of the aleatory clones, 17 marker.

Some aleatory clones were selected and digested with Eco RI and Hind III and a variety of different size inserts was presented (FIG. 3).

Example 4

Clone Sequencing for Mapping the Most Expressed Transcripts in the Salivary Gland of Ticks Based on the plates of the high weight library, 6 well plates were prepared by the alkaline lysis method and through it, 576 aleatory clones were sequenced.

Example 5

Clone Sequencing and "Primer" Outline

Among the obtained sequences some clones presented high homology with "Serpins" and among them one showed molecular mass characteristics similar to a serine protease inhibitor that had been previously purified from the saliva of the *A. cajennense* tick in the Laboratory of Biochemistry and Biophysics of Butantan Institute. This clone has its complete sequence presented in FIG. 4.

Example 6

Translation of the Clone Nucleotide Sequence into the Proteic Sequence

Using a program available at the Swiss Institute of Bioinformatics web-site, the nucleotide sequence of the selected clone was translated into the amino acid sequence. The sequence obtained is represented in FIG. 5.

Example 7

Sequence of the Mature Protein

The sequence obtained refers to the protein with the signal peptide, and by the cbs.dtu.dk/services/SignalP/ web-site it was possible the theoretical determination of this peptide, that was found between the positions 1 and 28 of this amino acid sequence. The sequence of the mature protein contains 108 amino acids, with theoretical molecular mass of 12,295.6 Da and theoretical isoelectric point (pI) of 4.67. The mature protein sequence is represented in FIG. 6.

Example 8

Sequence 5'-3' of the "Primer" Constructed for the Clone Amplification

Figures 7, 8:
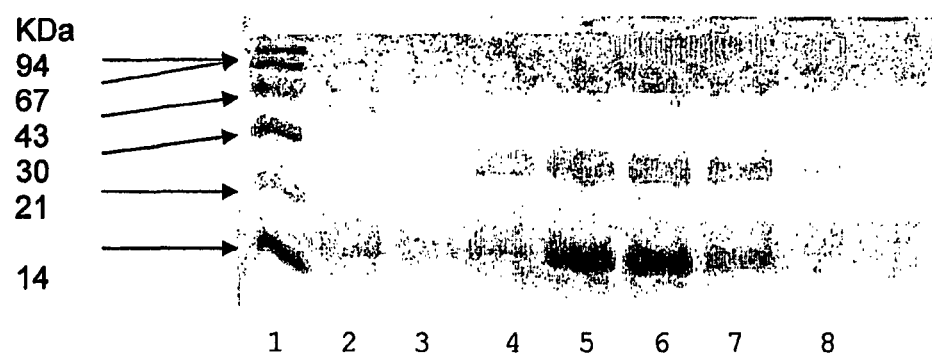
FIG. 7: Sequence 5'-3' of the "primer" constructed for the amplification of the clone selected for the expression (SEQ ID No.4).
FIG. 8: SDS-PAGE 15%. Purification of the recombinant inhibitor in Ni-Sepharose column. 1) marker of molecular mass, 2) Chromatography Entrance Material, 3 to 8) fractions eluded in the purification.

Based on the mature protein sequence a "primer" was outlined for the amplification of the interest inhibitor which also had a CTCGAG sequence that is a site for the Xho I enzyme, as FIG. 7 illustrates.

Example 9

Amplification of the cDNA that Codifies the Inhibitor

The amplification product obtained with the "primer" constructed and the SP6 "primer" presented a band of approximately 400 pb. This band was cut out of the gel and purified.

The purified cDNA was subcloned in vector and transformed into DH5α competent bacteria. The product was plated and from this procedure 20 aleatory selected clones were isolated and submitted to the extraction process by phenol-chloroform for the evaluation of insert presence.

Among the positive clones, 3 were selected for amplification, purification and were submitted to restriction essays with Xho I and Eco RI enzymes.

The clone sequence was confirmed and the insert liberated by the digestion was subcloned in the expression vector that inserts an end of six histidine residues in the N-terminus portion of the recombinant protein, expressed after the induction with IPTG.

The interest protein was found as inclusion corpuscle that after the urea and β-mercaptoethanol solubilization was purified in Ni-affinity column as SDS-PAGE demonstrate in FIG. 8.

The material eluded by chromatography in Ni-Sepharose was dialyzed against solutions with decreasing urea concentrations (until its absence). The material after dialysis was used in the structural essays and in the biochemical essays presented below.

Example 10

Comparative Example of Amblyomin-X and Ixodes Primary Structures

Based on the Amblyomin-X primary structure (deduced from the DNA sequence) a theoretical structural study of the molecule was conducted.

The Amblyomin-X presents around 17% of homology when compared to the TFPI-1 and approximately 18% to the TFPI-2, both in human cases. Besides that, structural studies demonstrated that Amblyomin-X presents around 21% of homology with Ixolaris, a recombinant protein that was cloned from the salivary glands of the *Ixodes scapularis* tick.

When the primary structures of Amblyomin-X and of Ixolaris are compared (GeneStream align) it is verified that Amblyomin-X presents a depletion both in the N-terminus portion between residues 3 and 13 (numbered according to the Ixolaris molecule) and in the C-terminus portion between residues 121 and 131, (11 amino acids). Besides that, residue depletions in the internal portion of the molecule (18 amino acids) occur, which are shown in FIG. 9.

The human TFPI, as already mentioned, presents 3 domains, D1 that is composed of residues 53 through 103, D2 composed of residues 124 through 174 and finally the D3 domain composed of residues 222 through 273. Therefore, the Amblyomin-X primary structure (with only 2 domains) was compared to each one of the domains of the human TFPI-I molecule.

In addition to that, the Amblyomin-X partial structures were submitted to the data banks and what was verified was that high "hits" of homology with Kunitz-type inhibitors are highly conserved for the N-terminus portion (residues 1-61: ANSKAVCNLP KLAGDETCSN KTEIRWYYNG TACEAFIFKG CGGNDNNFDRV DDCQRLCEEQ (SEQ ID NO:5)), however, the C-terminus portion (residues 62-108: THFHFESPKLI CFKVQDYWIL NDIMKKNLTGI SLKSEEEDAD SGEID (SEQ ID NO:6)), presents homology with the Phosphatase 2C type, Proteins of the Kinase System, Alpha-Amylase 3 and of the activators of the MAP-Kinase pathways, data obtained through a program of multiple alignments.

When analyzing the three-dimensional structure of the Amblyomin-X, obtained by molecular modeling, it presented a structural homology only with the first of the domains of the Kunitz-type inhibitors that are found in this Serpins family (Residues 1-61). Continuing the structural studies of the Amblyomin-X, its most probable secondary structure was analyzed through circular dichroism experiments and it could be seen that Amblyomin-X presents, out of 55% disordered structures, 10% of alpha helices and approximately 35% of beta-structures, data that corroborate with the modeling of this protein.

Example 11

Dosage of the Inhibitory Activity on FXa

In essays using a phospholipid mixture and also a fluorogenic substrate it was possible to verify the inhibition of FXa and the effect of dose-dependency as we can see in FIG. 10.

Example 12

Essays for Prolonging Coagulation Time

The recombinant inhibitor is able to prolong the coagulation time, either the time of thromboplastin partial activated (TTPA) and the time of prothrombin (TP). FIG. 11a shows the TTPA prolonging was from 43.4 seconds (control) to 137.5 seconds in presence of 50 ug of the recombinant inhibitor, what reflects an inhibition of 60%. FIG. 11b shows the prolonging of TP from 14.3 seconds in absence of the inhibitor to 89.3 seconds in presence of 50 ug of the recombinant inhibitor reflecting a theoretical inhibition of approximately 85%.

Example 13

Amblyomin-X Action in Coagulation Time in Presence of Phospholipids

Figure 12:
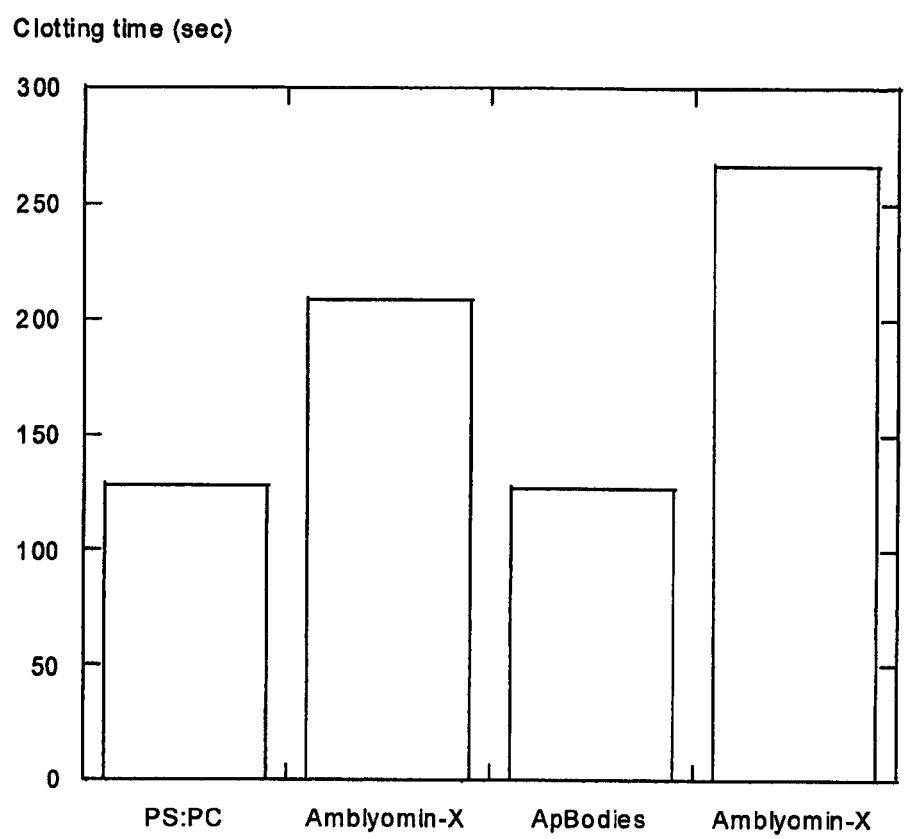
FIG. 12: Coagulation time using PS: PC or apoptotic bodies in presence and absence of Amblyomin-X.

It could also be observed that in coagulation essays where phospholipids were substituted by apoptotic bodies produced in CHO (Chinese Hamster Ovarian) cells, the coagulation time changed from 129 seconds (control) to 210 seconds in presence of 2.5 uM of Amblyomin-X as can be seen in FIG. 12. There we can observe Amblyomin-X capacity in inhibiting the pro-coagulant effect of apoptotic bodies.

Example 14

Cytologic Aspects Caused by Amblyomin-X in B16F10 Cells, 6 Hours after Treatment: Analysis of the Morphologic Alterations and Cytotoxicity The tumoral cells of B16F10 melanoma treated with different concentrations of Amblyomin-X were cultivated in plates of 96 wells. The cytotoxic alterations and adhesion loss were firstly observed cytologically, and images were achieved by the Capture System.

Figure 13:
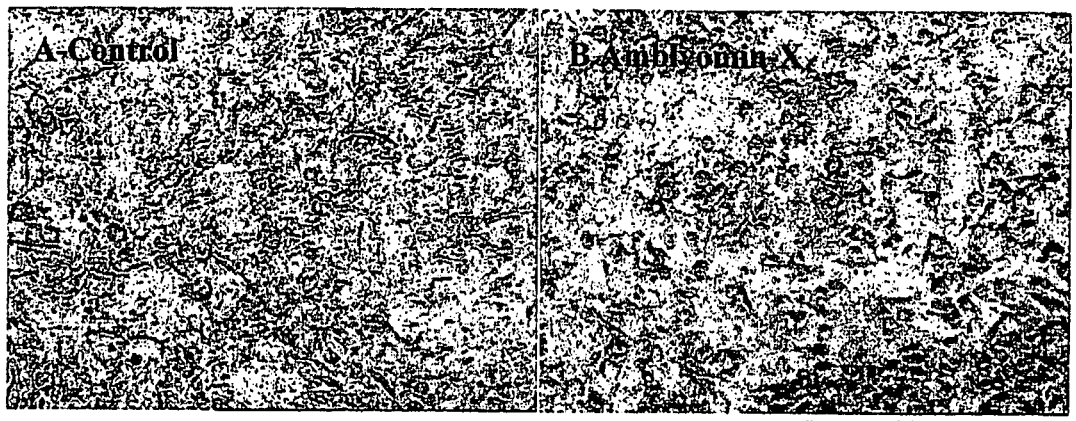
FIG. 13: Cytological aspects of the alterations provoked by the treatment with Amblyomin-X (0.3 uM) in B16F10 cells after 6 hours.

The treatment of cellular cultures of B16F 10 murine melanoma with Amblyomin-X presents cytotoxic effect of time and dose dependent manner. The cultures of B16F10 cells treated with 0.5 uM of Amblyomin-X after 6 hours showed small and discrete cytoplasmatic alterations as vacuolization and contractions of intercellular prolonging without presenting detachment of the tumoral cells. Significant cellular adhesion loss was not observed. Data can be seen in FIG. 13.

Example 15

Figure 14:
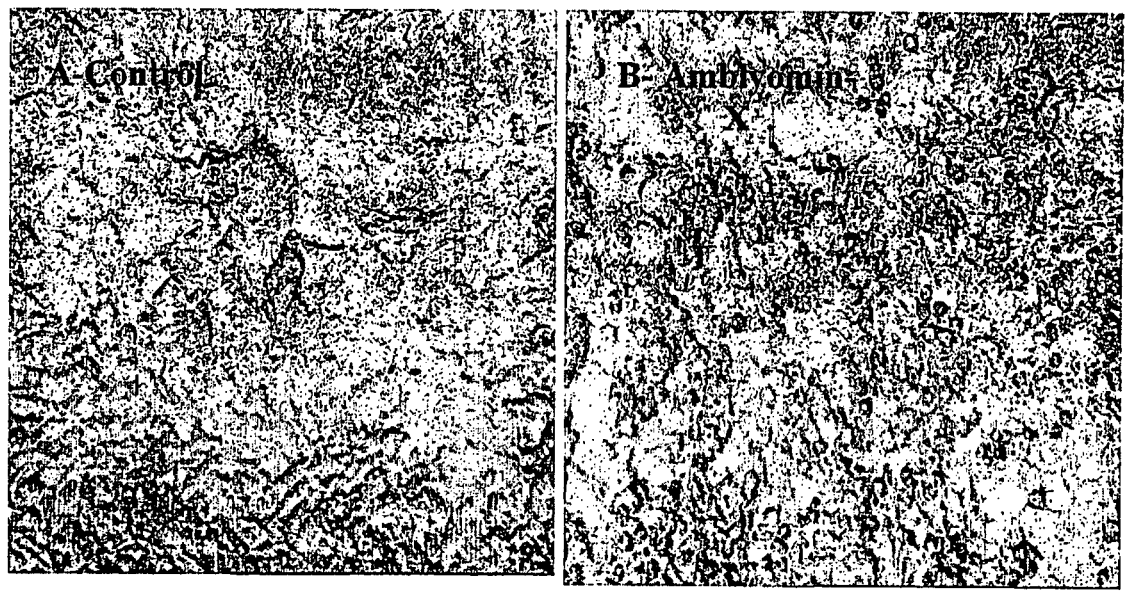
FIG. 14: Aspects of cytological alterations provoked by Amblyomin-X (0.3 uM) in B16F10 cells after 12 hours of treatment.

Aspects of the Cytologic Alterations in B16F10 Cells, 12 Hours after Treating with Amblyomin-X After 12 hours exposing melanoma cells to 0.5 uM of Amblyomin-X, moderate alterations were observed concerning the contraction of intercellular prolonging with the formation of cellular aggregations dispersed in the culture supernatant as can be seen in FIG. 14.

Example 16

Figure 15:
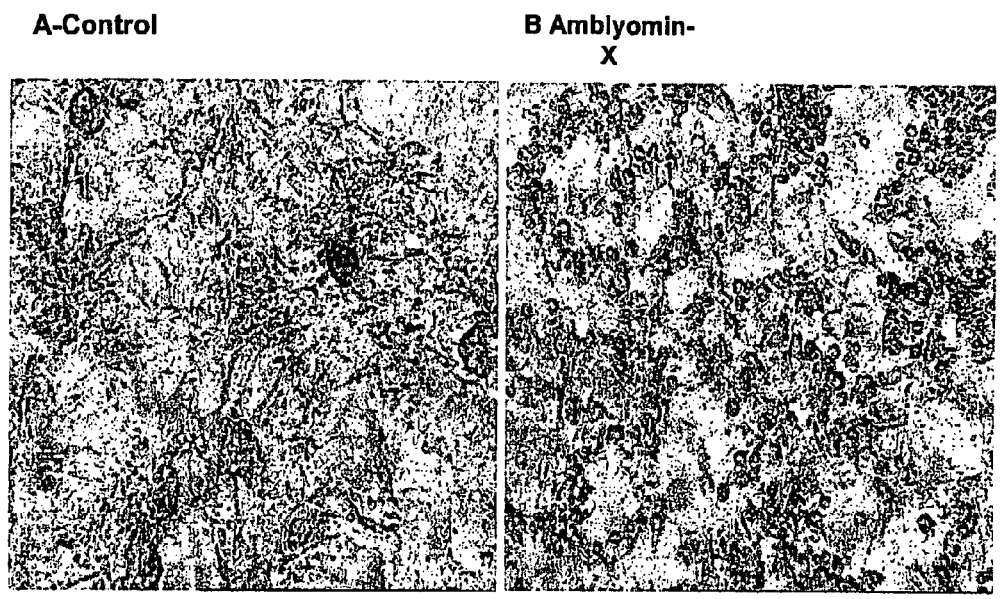
FIG. 15: Aspects of the cytological alterations provoked by the Amblyomin-X (0.3 uM) treatment in B16F10 cells after 24 exposing hours.

Aspects of Cytology Alterations Caused in B16F10 Cells 24 Hours after Treating with Amblyomin-X After 24 hours treating B16F10 tumoral cells with 0.5 uM of Amblyomin-X, the cells presented significant alterations in the contraction and adhesion as well as several cellular aggregations were reduced, as observed in FIG. 15.

Example 17

Figure 16:
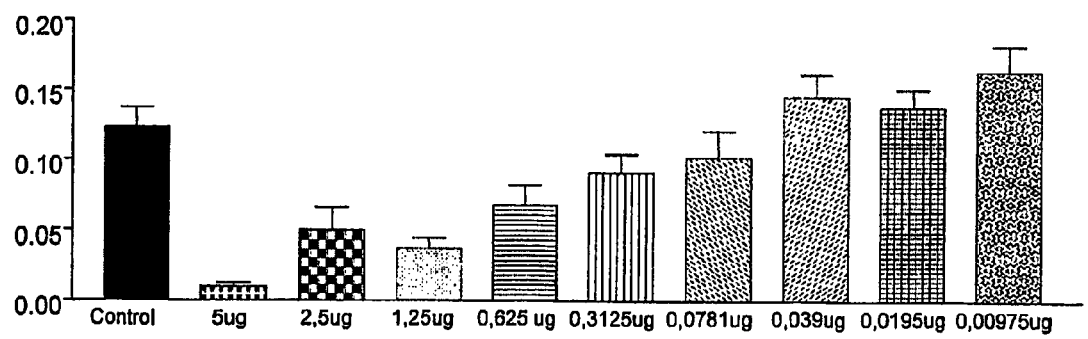
FIG. 16: Analysis of the cellular adhesion inhibition of B16F10 melanoma cells treated with different concentrations of Amblyomin-X.

Analysis of the Inhibition of Cellular Adhesion of B16F10 Melanoma Cells Treated with Different Concentrations of Amblyomin-X After 24 hours of B 16F10 cells culture in presence of different concentrations of AMBLYOMIN-X (0.3 uM to 0.1 nM) in culture plates of 96 wells, a loss of 55% of the adhesion to the substrate of the cells was observed and it showed to be dose dependent (FIG. 16).

Example 18

Effect of Amblyomin-X on the Viability of B16F10 Melanoma Cells

Figure 17:
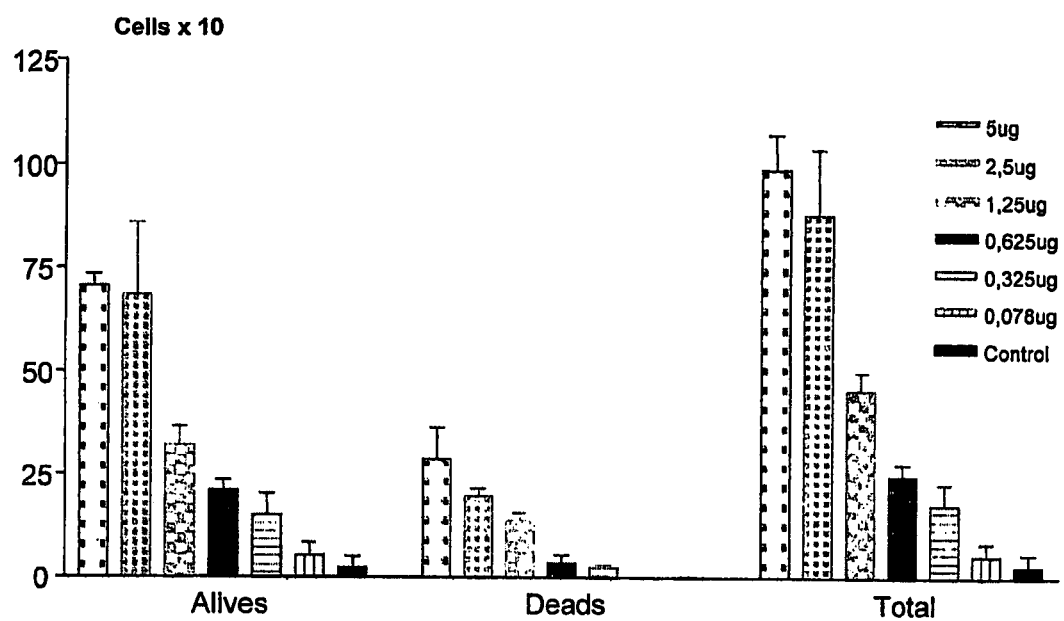
FIG. 17: Amblyomin-X effect on the viability of the B16F10 melanoma cells.

Viability loss was observed in concentrations from 0.3 uM to 0.1 nM. The supernatant was collected; the number and cellular viability were determined by the exclusion test with Blue Trypan. The cellular concentration was determined in Mallassez haemocytometric Chamber. In these concentrations the viability was also dose dependent, over 75% when 5 ug was used. It showed the highest percentage of cellular detachment, as can be seen in FIG. 17.

Example 19

Analysis OF B16F10 Dorsal Melanoma Growing in C57BL/6J Mice Treated with Amblyomin-X $2.5 \times 10^5$ B16F10 tumoral cells were injected in mice by subcutaneous route and after the $12^{th}$ day, 1 mg/kg of Amblyomin-X was injected in animals with dorsal tumor by subcutaneous administration until the $14^{th}$ day. The same volume of saline solution was administered by the same route in animals of the control group after the $12^{th}$ day of inoculation of the tumoral cells.

Figure 18:
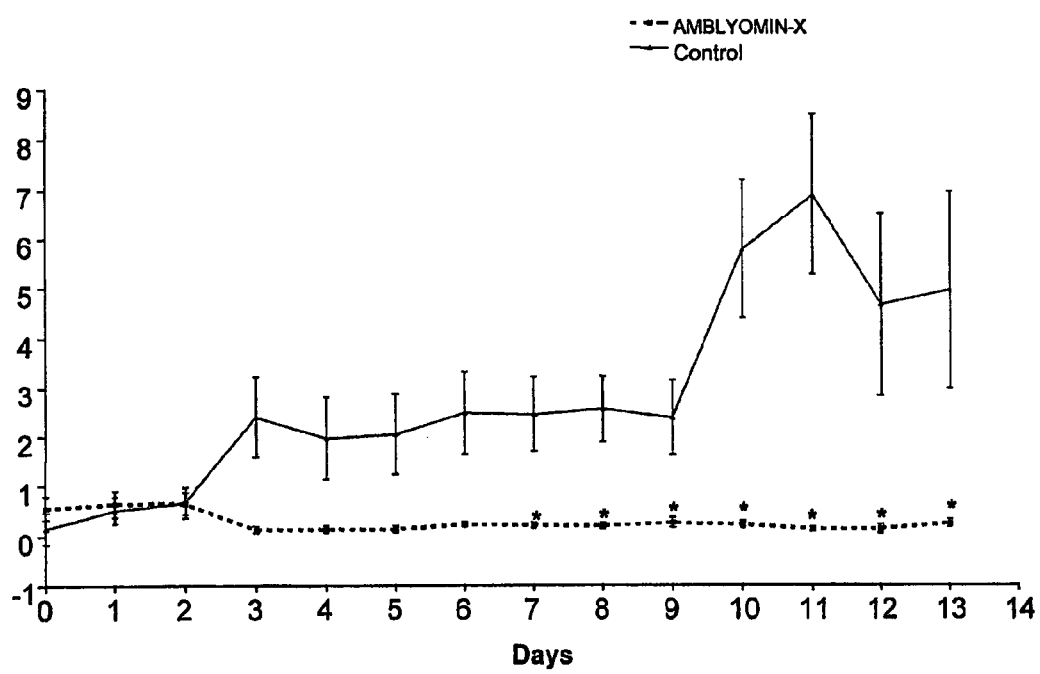
FIG. 18: analysis of the growing of B16F10 dorsal melanoma treated with AMBLYOMIN-X during 14 days.

The animals were daily observed and the diameter of the tumor determined through a pachymeter. The animals treated with Amblyomin-X presented a significant decrease of the dorsal tumoral volume when compared to the control group (FIG. 18).

Figure 19:
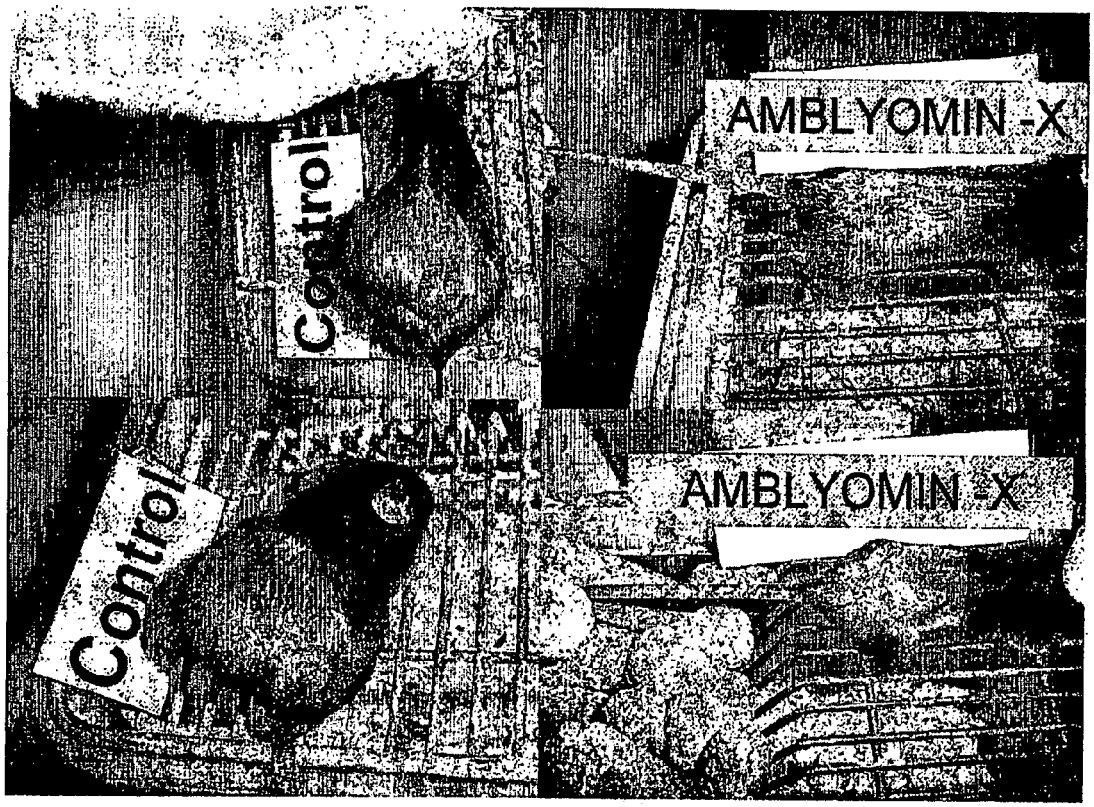
FIG. 19: Macroscopic aspect of dorsal tumors produced after the implantation of B16F10 melanoma cells and treated with 1 mg/Kg of Amblyomin-X during 14 days.
Figure 20:
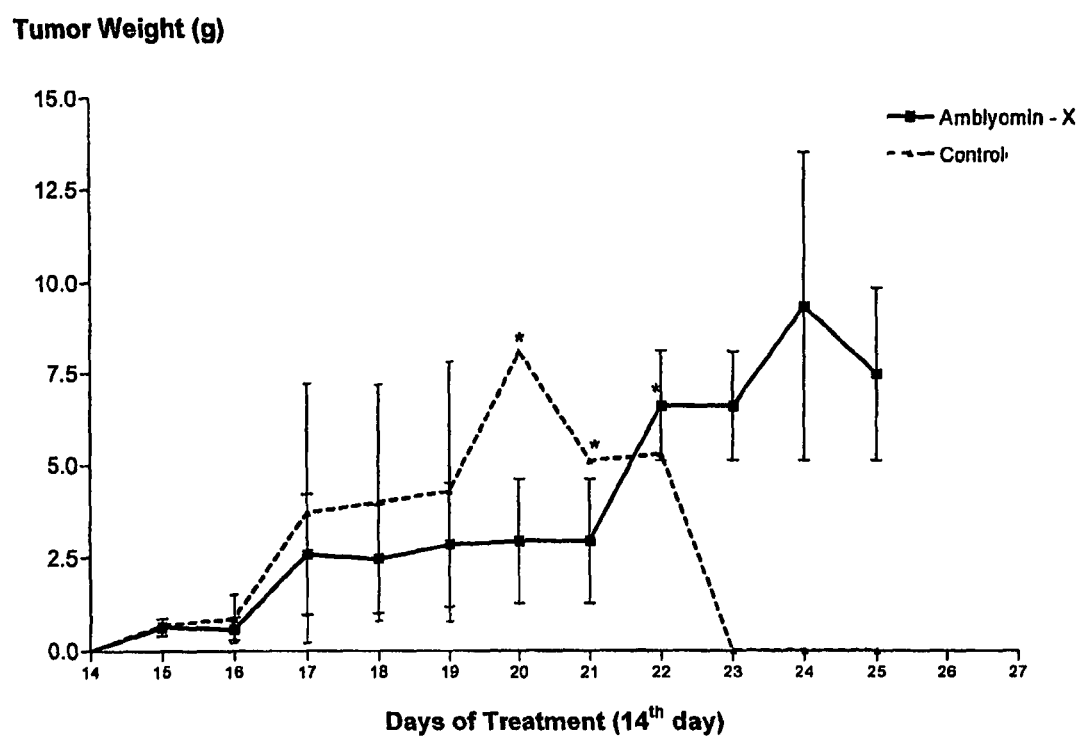
FIG. 20: Growing curve of tumoral weight after the treatment with Amblyomin-X.

In treated animals, macroscopically evaluated, the dorsal tumors were smaller concerning pigmented and average volumes. On the other hand, tumors of the control group were extremely large, nodular, ulcerated, with extensive necrosis area. The animals injected with tumoral cells and not treated, presented high levels of cachexia during the treatment (FIG. 19). The life lasting rate (accumulative %) of the treated group compared to the non-treated (control) was in average of 13 days. The animals treated with Amblyomin-X presented normal aspects (FIG. 20).

Example 20

Number of Tumoral Nodules Present in Pulmonary Parenchyma after Treating with Amblyomin-X C57BL/6J mice groups received $5 \times 10^4$ tumoral cells, by endovenous route, and after the $12^{th}$ day of the injection they were submitted to treatment with 0.5 mg/Kg of Amblyomin-X. This treatment was daily administered by intraperitoneal route during 14 days and the animals were daily observed.

Figure 21:
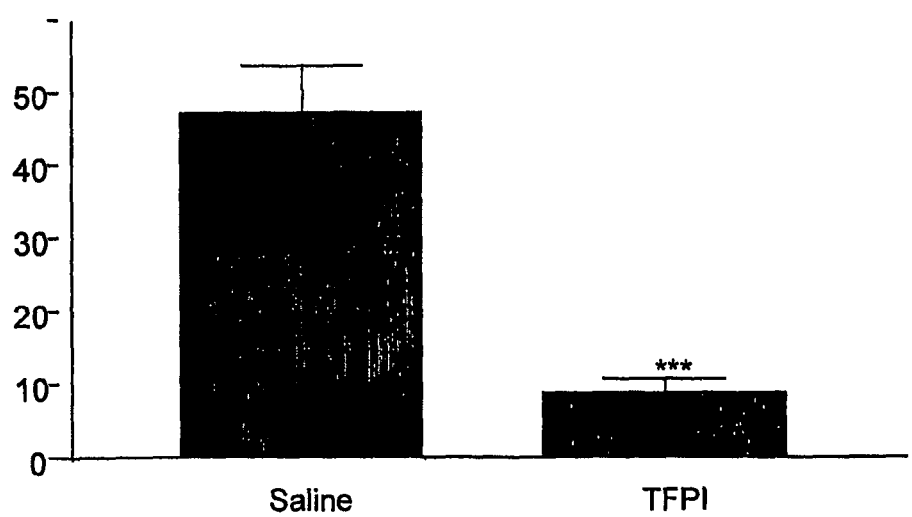
FIG. 21: Number of tumoral nodules present in pulmonary parenchyma after treating with Amblyomin-X for 14 days.

After necropsy, the animals treated with Amblyomin-X, presented a highly significant reduction in tumoral nodules number present in the pulmonary parenchyma compared to that of the control group (FIG. 21).

Example 21

Size Distribution of the Pulmonary Lesions after Treating with Amblyomin-X

Figure 22:
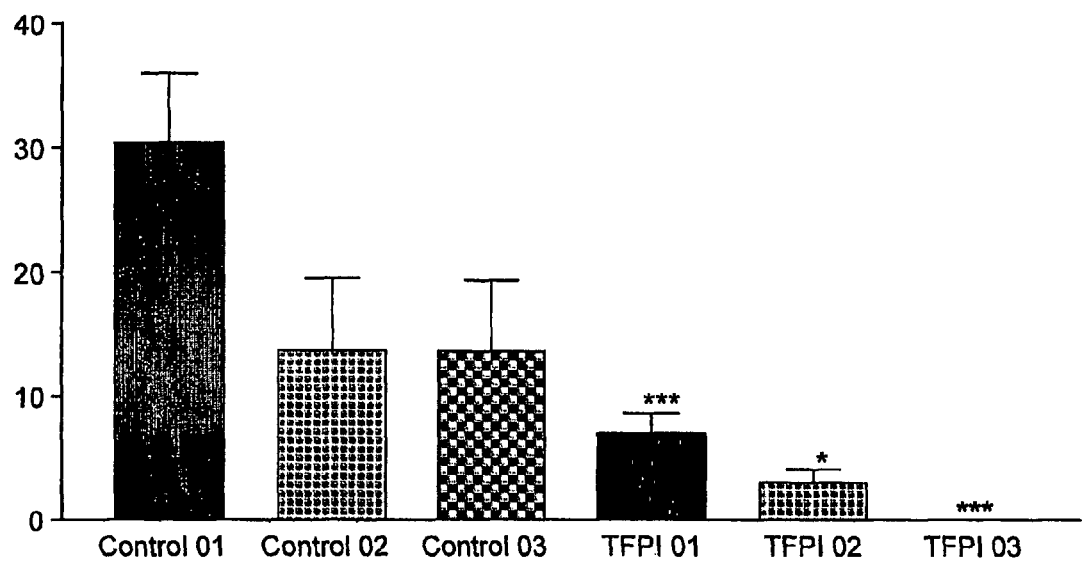
FIG. 22: Size distribution of pulmonary lesions after the treatment with Amblyomin-X.

The macroscopic analysis of the pulmonary parenchyma revealed that the average diameter of the nodules present in the control group varied from 0.1 to 0.3 cm. In animals treated with Amblyomin-X not only they showed reduced number of lesions (low multiplicity) but they also did not present lesions larger than 0.3 cm. It could also be observed that the diameter ranged between 0.1 and 0.2 cm without showing invasion or dissemination characteristics (FIG. 22).

Example 22

Figure 23:
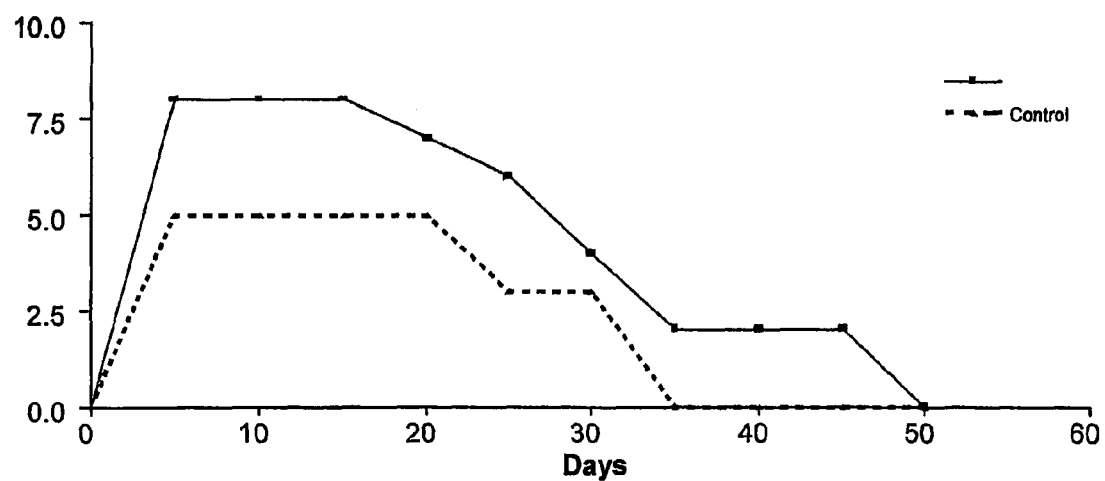
FIG. 23: Analysis concerning the life lasting rate of animals with pulmonary parenchyma metastases treated with Amblyomin-X.

Analysis of the Life Lasting Rate of Animals with Metastases in the Pulmonar Parenchyma Treated with Amblyomin-X The life lasting rate (expressed in accumulative %) of animals with pulmonary metastases treated with Amblyomin-X compared to those of control group (non-treated) was 15 days. (FIG. 23).

Weight loss of animals treated with Amblyomin-X was not observed during the therapeutic protocol and the increase of tumoral mass after this period was not seen either.

Example 23

Macroscopic Aspect of Dorsal Tumors of Melanoma in B16F10 Mice Treated During 42 Days with Amblyomin-X B16F10 animals with dorsal tumor received daily treatment with 1 or 0.5 mg/Kg of Amblyomin-X after the $3^{rd}$ day followed the injection of the tumoral cells. The animals with tumor were daily treated by subcutaneous administration for 42 consecutive days.

The results showed that the treatment is efficient with a significant reduction of tumoral mass and volume in treated animals compared to those of the control group.

It was observed that animals with injection of tumoral cells did not present tumoral growing or even tumoral mass disappearance was observed probably by the induction of tumor remission. A group of animals was dissected and the existing tumors were macroscopically small, pigmented, not nodular and not presenting necrosis areas. It could also be seen that tumor irrigation was not increased and it did not present system recruitment of peripheral vessels adjacent to the lesion. Neo-angiogenesis was not observed either (FIG. 24).

Example 24

Macroscopic Aspect of the Dorsal Tumor of B16F10 Melanoma of C57BL/6J Mice (Control Group and Treated for 42 Days)

The histopathologic aspects of dorsal tumors of the control group that received saline solution during the therapeutic protocol showed high cellularity tumoral mass similar to the sincicial mass with extended area irrigated by average and small vessels as well as capillary vessels. Around the tumoral mass a discrete inflammatory infiltration of monomorphonuclear leukocytes was observed. Tumors of groups treated with Amblyomin-X (1 mg/Kg) taken after the $14^{th}$ day of treatment showed tumoral mass with low proliferative activity, low amount of sustentation fibril elements (few connective tissue/stroma) without occurring peritumoral inflammatory infiltration. The pulmonary metastatic lesions of this group showed to be of small tumors with low cellularity, in the pulmonary parenchyma, presenting alveoli thickness and deposition and brownish pigment of melanin type. Bronchial intraseptal inflammatory infiltration was not observed in these lesions. The dorsal tumors obtained from the animals treated with AMBLYOMIN-X during 42 days showed that the tumoral cells are organized like in islands permeated by extensive necrosis areas (FIG. 25B), differently than the control (FIG. 25 A). By the haematoxylin/Eosin stain technique, neo-formed blood vessels were not detected. The other internal organs analyzed, as: kidneys, liver, spleen and heart did not present histologic alterations. Functional loss or direct toxicity effects in these organs caused by the prolonged treatment with Amblyomin-X were not observed.

The formation of a small amount of material showing fibrinilar or exudative aspect around the tumoral mass was observed.

Example 25

Figure 26:
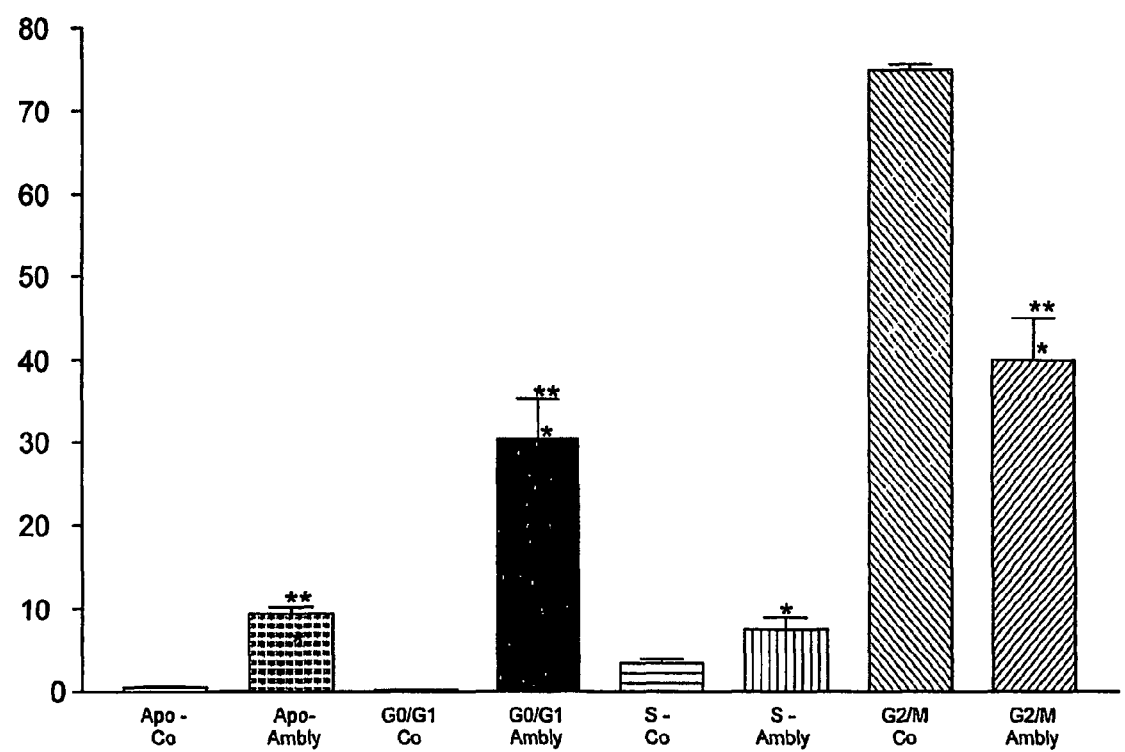
FIG. 26: Phase analysis of the cellular cycle of B16F10 melanoma dorsal tumors treated with Amblyomin-X.

Analysis of the Cellular Cycle Phases of the Dorsal Tumor Cells of B16F10 Melanoma of Mice Treated with Amblyomin-X Evaluation of the cellular cycle phases: After the necropsy of the animals with dorsal tumor or with pulmonary metastases treated during 14 days with Amblyomin-X and of the control group animals that received saline solution, the cellular cycle phases of the tumors were evaluated by flow cytometry and the percentages of the cells were determined in phases sub G1 or apoptotic, G0/G1, Phase S and G2/M. The results showed that the tumoral cells obtained from the dorsal tumor of animals that received treatment with Amblyomin-X presented mostly in apoptosis phases (sub-G1) and quiescent (G0/G1) and with low proliferative activity (G2/M) (FIG. 26)

Example 26

Figure 27:
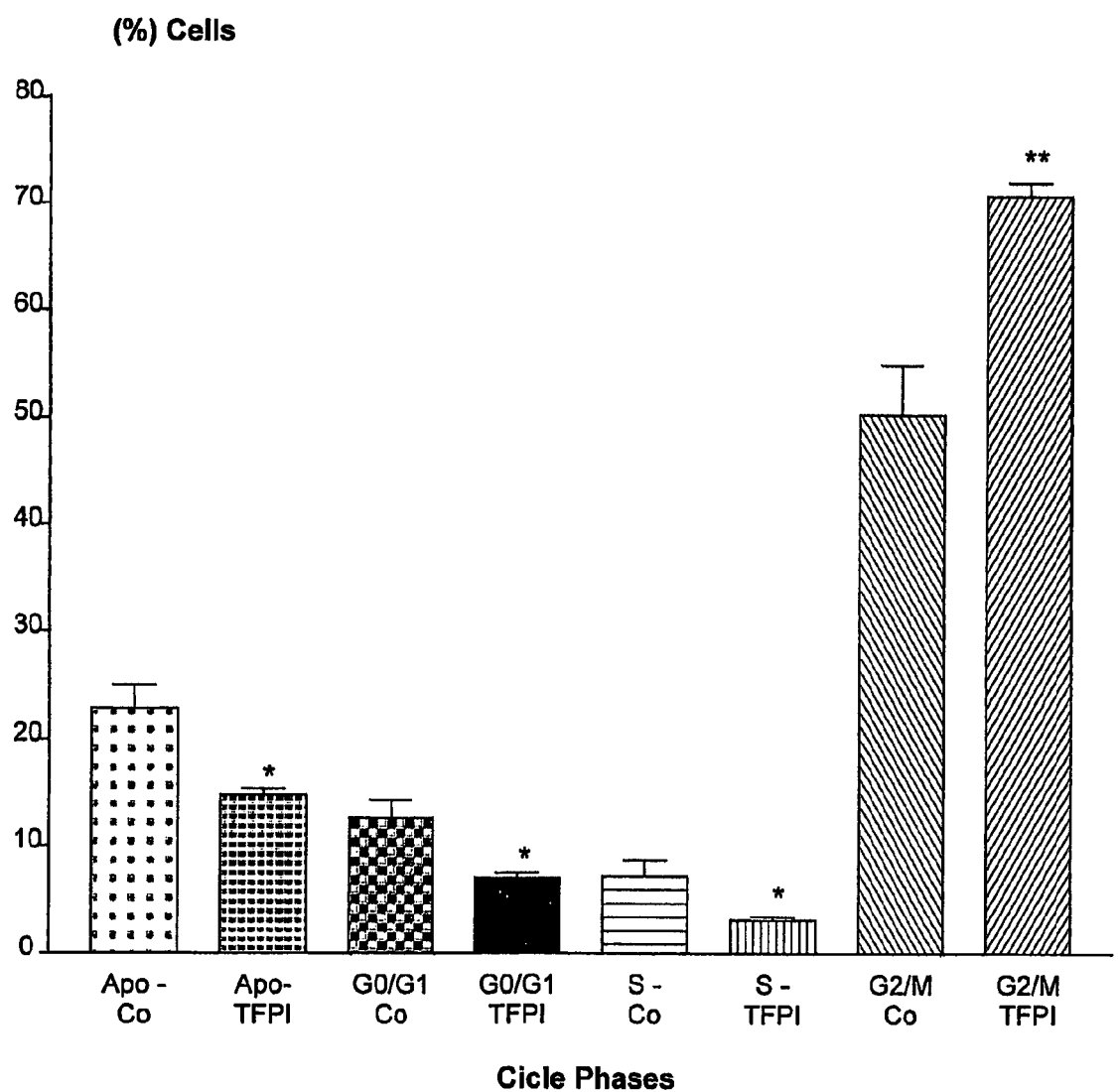
FIG. 27: Phase analysis of the cellular cycle of pulmonary metastases of the animals treated with Amblyomin-X.

Analysis of the Cellular Cycle Phases of Metastatic Lesions OF B16F10 Melanoma of Animals Treated with Amblyomin-X The cells obtained from lesions of the pulmonary metastases analyzed by flow cytometry were in significant number in phase G2/M of the cellular cycle representing a blockage of the proliferative capacity of these cells and the treatment efficiency (FIG. 27).

Example 27

Figure 28:
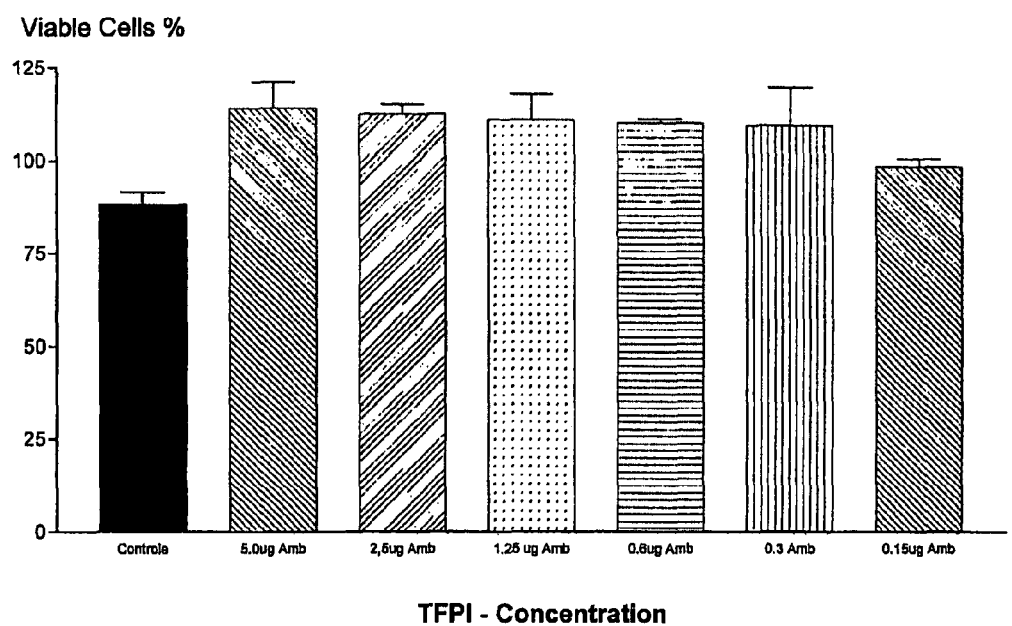
FIG. 28: Cytotoxicity determination of healthy human lymphocytes treated with different concentrations of Amblyomin-X.
Figure 29:
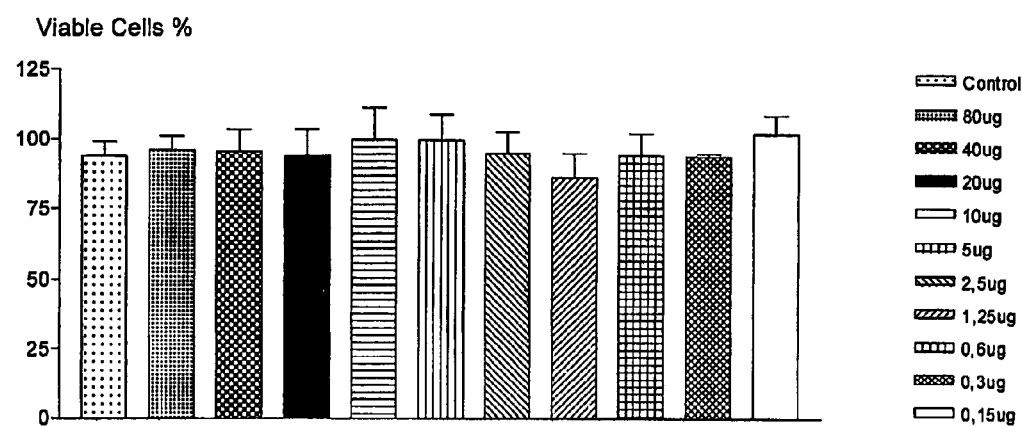
FIG. 29: Determination of the cytotoxic effects of the low molecular weight heparin in B16F10 cells and SKMEL-28.
Figure 29:
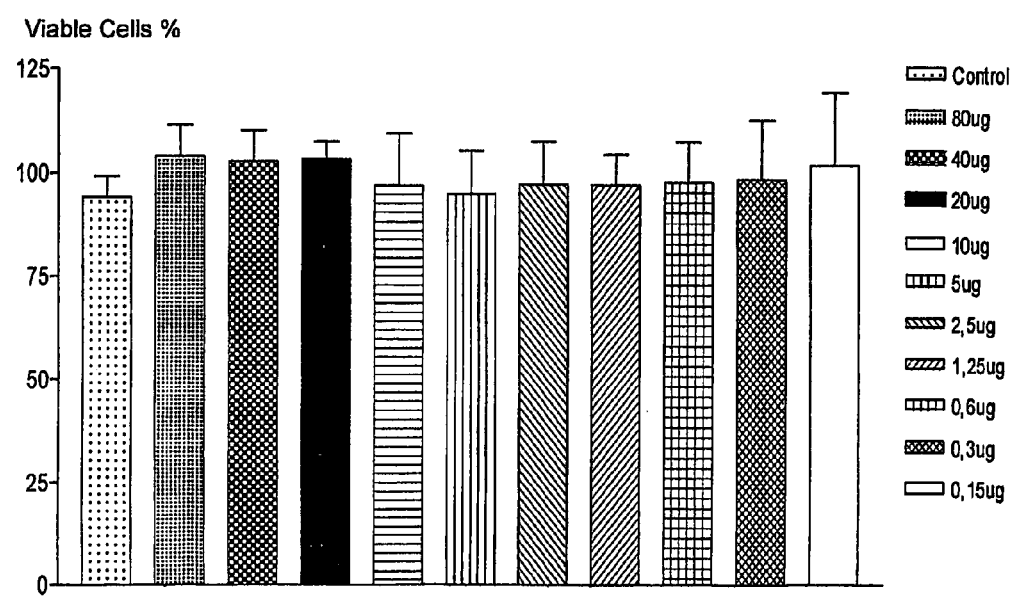

Cytotoxicity Determination of Different Concentrations of Amblyomin-X in Healthy Human Cells Exposing healthy murine and human cells to different concentrations of Amblyomin-X for 24 hours showed that for skin fibroblasts, lymphocytes, macrophages and neutrophils, Amblyomin-X did not present cytotoxic effects and no cellular death or cells detachments in the culture plate (FIG. 28) were observed when compared to the heparin treatment (FIG. 29).

Example 28

Figure 30:
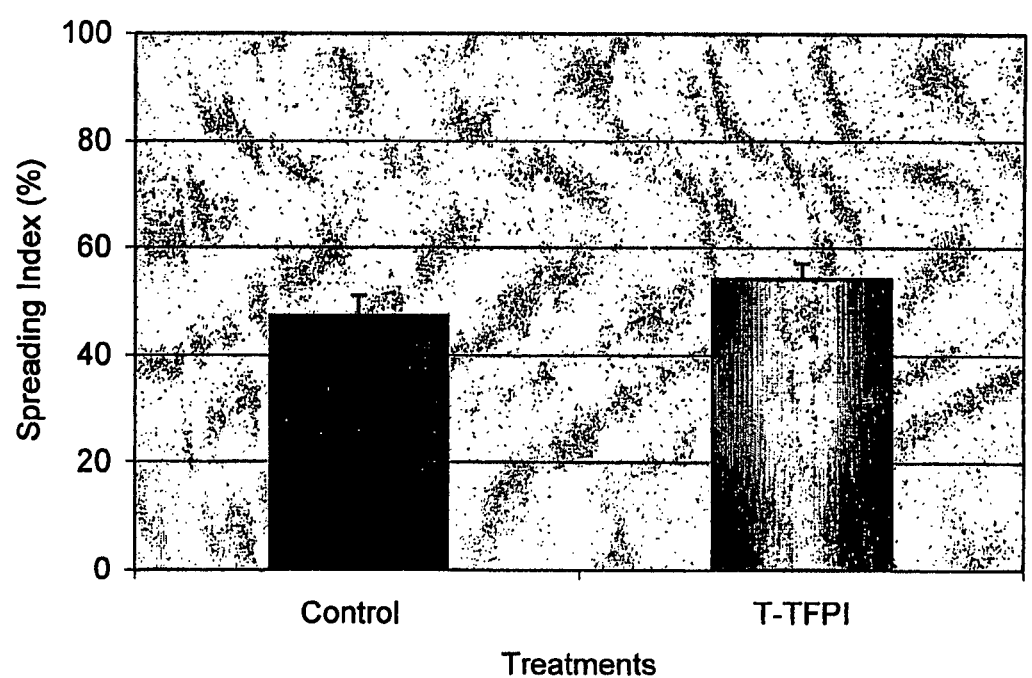
FIG. 30: Spreading of peritoneal macrophages after 1 h of treatment with 0.3 uM of Amblyomin-X.
Figure 31:
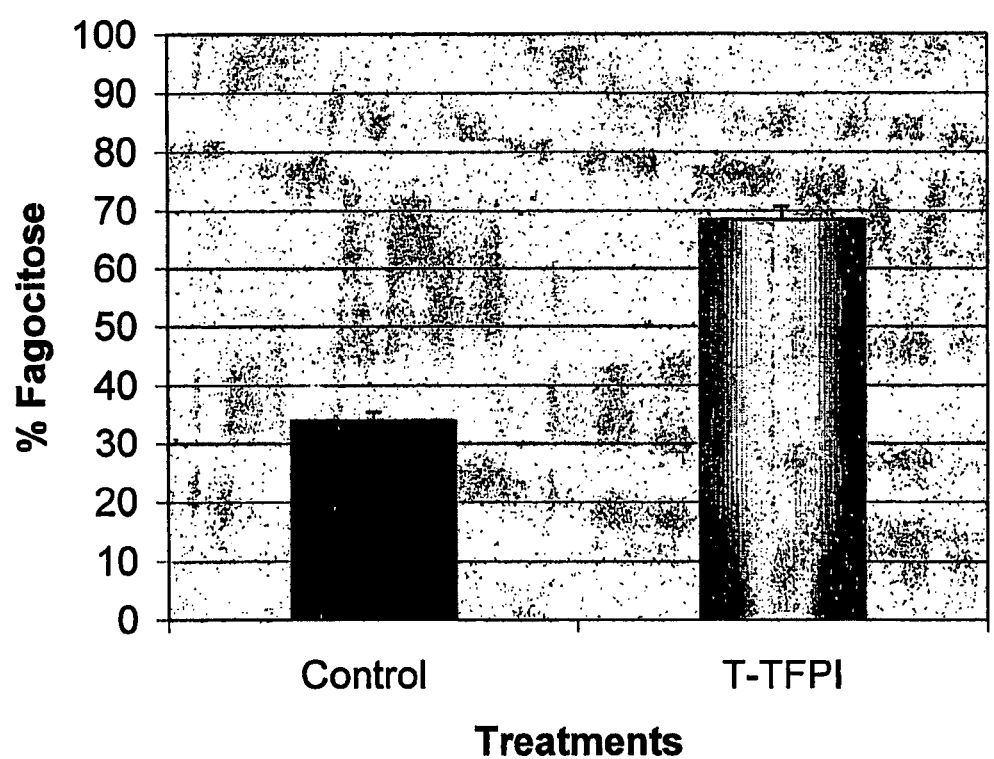
FIG. 31: Phagocytic index of peritoneal macrophages after 1 h of treatment with 0.3 uM of Amblyomin-X, measured by C3b of the complement.
Figure 32:
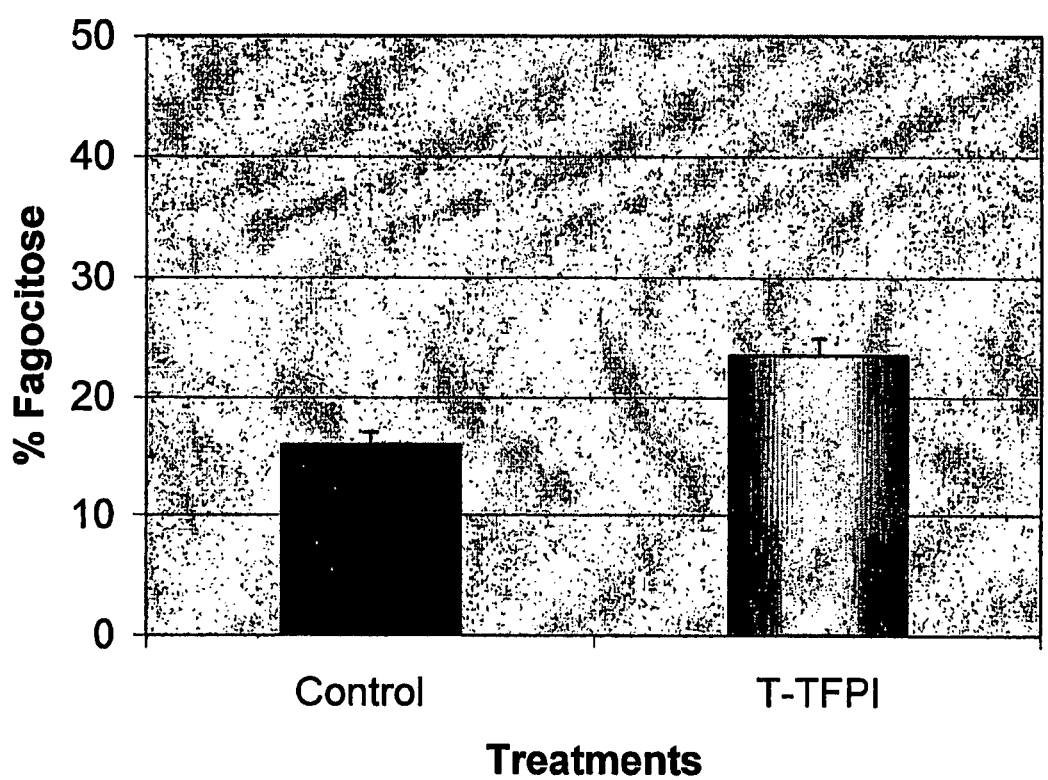
FIG. 32: Phagocytic index of peritoneal macrophages after 1 hour of treatment with Amblyomin-X mediated by the Fc portion of the antibody.

Evaluation of the Macrophages Functional Activity of Animals with B16F10 Melanoma and Treated with Amblyomin-X The functional activity evaluation of macrophages in animals with B16F10 melanoma treated with Amblyomin-X and in the control group showed that the treatment increases the phagocytary activity of the macrophages and this activity is dependent of the C3b fragment of the complement system or of the Fc receptor of the immuno-globulin (FIG. 30, 31 e 32).

Example 29

Coagulation Tests

The time of thromboplastin partial activated (TTPA) and the time of prothrombin (TP) was evaluated in presence and absence of Amblyomin-X. For conducting these tests, commercial coagulation "kits" were used.

TTPA is the test in which the intrinsic route of coagulation is evaluated, that is, the plasmatic callicrein and factors XII, IX, XI and X were monitored.

The essay control was conducted in absence of the Amblyomin-X and consisted of one incubation during 3 min at 37° C. of 100 ul of healthy human plasma, 100 ul of cefaline and 100 ul of tris HCl 0.1 M pH 8.0 buffer, followed by the medium re-calcifying by the addition of 100 ul of $CaCl_2$ 0.025 M.

The time of the clot formation was measured by a semi-automated coagulometer. In case of inhibition experiments instead of buffer, 100 ul of Amblyomin-X solution prepared in tris HCl 0.1 M pH 8.0 buffer was used.

For the other coagulation test, TP, the same equipment was used. TP verifies the coagulation extrinsic route, that is, it monitors factors II, V, VII and X.

The control of the essay was conducted incubating for 2 min at 37° C., 100 ul of plasma with 100 ul of tris-HCl 0.1 M pH 8.0 buffer and for adding afterwards 100 ul of the reagent. The clot formation time was measured just like the test mentioned before. Instead of the buffer, 100 ul of Amblyomin-X solution prepared in tris HCl 0.1 M pH 8.0 buffer was incubated for evaluating inhibition.

The Amblyomin-X effect, in the coagulation time, using apoptotic bodies produced in CHO cells as source of phospholipids, was also verified.

Example 30

Amblyomin-X Action on the Pro-Coaguiant Effect of Apoptotic Bodies

A curve was idealized for standardizing the coagulation test named PCA "Pro Coagulant Activity" and toward this, 3-min pre-incubation at 37° C. was conducted for a final volume of 60 ul of Factor VII activated (FVIIa) 1 nM with Factor X human (FX) 0.25 and $CaCl_2$ 8.3 mM with different concentrations of recombinant tissue Factor (r-TF) (1.56-12.5 ng/ml) in Hepes 250 mM buffer containing bovine albumin (BSA) (1%). After that, 100 ul of a mixture containing normal human plasma (87.5 ul), phosphatidyl serine: phosphatidyl choline PS 30: PC 70 (7.5 ul) and Hepes (50 in M) were added and the mixture was incubated for another 3 minutes. The reaction started by adding 20 ul of $CaCl_2$ 250 mM.

Amblyomin-X was pre-incubated with apoptotic bodies produced in CHO cells and it was observed that the coagulation time induced by the apoptotic bodies was prolonged (Sorensen et al., 2003).

Example 31

Evaluation of the Amblyomin-X Anti-Tumoral Capacity on Culture of Human and Murine Tumoral Lineages The tumoral lineages: HL-60, K562, U937, YAC-I, JURKAT, Mel-85, Mewo, MCF-7, SW613-12A1, SW613-B3, the SW613-12A1 and SW613 colon cancer lineages and the B16F10 murine melanoma lineage were cultivated in culture bottles of 75 cm3 in RPMI-1640 medium supplemented with 10% of bovine fetal serum, 2 mM L-glutamin, 1 mM sodium pyruvate and streptomycin 0.1 mg/ml and ampicillin 0.1 mg/ml antibiotics. Before reaching confluence (adherent cells), the cells were cultivated for amplifying and maintenance lineages, frozen in RPMI-1640 culture medium containing 10% dimethyl-sulphoxide and maintained in liquid nitrogen.

The suspensions of adherent cells (B16F10, SW613-12A1, SW613-B3 and MCF-7) for all the experimental procedures were obtained by the treatment of the culture bottles with trypsin 0.2% for 5 minutes and inactivation with 10% bovine fetal serum. The detached cells were centrifuged twice, re-suspended in RPMI-1640 supplemented medium. The cells counting was conducted in Malassez chamber and the cellular concentration was adjusted in $5 \times 10^5$ cells/ml in RPMI-1640 medium supplemented with 10% of bovine fetal serum and 7 ug of Polymixine-B.

The cellular viability was determined by the exclusion test of Blue Trypan showing over 95% of viable cells.

Example 32

Treating Tumoral Cells with Amblyomin-X

The $2 \times 10^5$ concentration cells were cultivated in plates of 96 wells, maintained for 24 hours in CO2 sterilizer at 37° C. After this period the plates were centrifuged for 5 minutes in 2000 rpm at 4° C., the supernatant was excluded and different concentrations of Amblyomin-X were added from 0.3 uM to 0.3 nM, diluted in RPMI-1640 culture medium, supplemented and added with 7 ug of Polymixine-B. After 6, 12 and 24 hours the cytological alterations were observed and photo-documented in image capturing system.

Cellular Cycle

The flow cytometry applied in the study of cellular cycle registers the kinetic parameters of the cells showing the DNA index, the ploidia, the cellular proliferation fraction and the percentage of cells found in phases S and G2/M, indicating uni or multivariable parameters for prognosis and possible therapeutic procedures. The analysis of the percentage of cells provides the percentage of cells that are synthesizing DNA ("labeling index"), duration of phase S (Ts) and the time of potential duplication (Tpot).

Example 33

Determination of DNA Content

Aliquots of the suspensions of tumoral cells treated and non-treated with Amblyomin-X were immediately frozen in buffer of citrate (2 mM), sucrose 25 mM and dimethyl sulphoxide, 0.05% and maintained in liquid nitrogen up to the moment it was used.

After defrosting the samples in ice bath, the cells were incubated with 375 µl of trypsin 0.03 g/l for 10 minutes at room temperature and neutralized with the inhibitor of trypsin 0.5 g/l, ribonuclease A 0.1 g/l and spermine 1.2 g/l. The samples were transferred to tubes of flow cytometry and the number of cells in different phases of the cycle, the apoptosis level (Sub-G1) and the DNA content in phase S were analyzed.

Example 34

Determination of Cellular Cycle Phases

Cellular suspensions ($10^6$/ml) of normal cells and of the tumoral lineages were centrifuged twice for 3000 rpm at 4° C. with PBS solution and re-suspended in 200 µl solution of propidium iodide (20 µl/ml), containing 20 µl Triton X-100 and 4 mg RNAse-A, for thirty minutes at room temperature protected from light. After this period the samples were transferred to cytometry tubes and the images were captured in Flow cytometer. The cellular cycle phases of pre and post-mitotic (G0-G1, phase S and G2-M) were analyzed.

Example 35

Culture of Tumoral Lineages and Tumoral Implantation in Animals (Mice)

The adherent cellular suspensions (B16F10) used for the implantation in the dorsal flank of the animals were obtained after treating the culture bottles with trypsin 0.2% for 5 minutes and inactivating with bovine fetal serum 10%. The detached cells were centrifuged (2.000 rpm) twice and re-suspended in RPMI-1640 medium supplemented with 10% bovine fetal serum inactivated at 56° C. for 1 h, 2 mM L-glutamin, 1 mM sodium pyruvate and streptomycin 0.1 mg/ml and ampicillin 0.1 mg/ml antibiotics. The cells counting was conducted in Malassez chamber and cellular concentration adjusted for $5 \times 10^4$ cells/ml.

Example 36

Growing of Primary Dorsal Tumors and Evaluation of the Internal Metastases

Groups of 10 mice, maintained in the laboratory animal care facilities, belonging to the C57BL/6J lineage were used. The animals were kept with light/dark 12-hour cycles, at constant temperature of 20° C., filtrated and sterilized water and food "ad libitum".

For the growing experiments of primary dorsal tumors, $2.5 \times 10^4$ tumoral cells of B16F10 murine melanoma were injected in the dorsa of mice (groups of 10 animals) by subcutaneous route. For evaluating the internal metastases, groups of C57BL/6J mice received $5 \times 10^4$ B16F10 tumoral cells by endovenous route through the ocular retro-orbital venous plexus. After the $12^{th}$ day of the inoculation this group of animals was treated with 0.5 mg/Kg of Amblyomin-X, administered by intraperitoneal route, and observed until the $14^{th}$ day of the treatment.

Animals that received tumoral cell by subcutaneous route presenting dorsal tumors after the $12^{th}$ day were treated with 1 mg/Kg of Amblyomin-X. They were observed daily until being anesthetized and killed where their tumors were measured using a pachymeter. Tumors presented an average diameter of 0.5 cm. The treatment with Amblyomin-X was started.

As control group, the animals received saline solution by the same route of the treatment and after the $14^{th}$ day of treatment. The animals were anesthetized and killed by cervical dislocation. Necropsy was conducted and the dorsal tumors were analyzed, the macroscopic internal lesions identified, measured and photo-documented. Samples of the tumors of the different groups of treatment and of the control group, non-treated, were processed for analyzing the contents of DNA, cellular cycle and anatomopathologic.

Example 37

Observing Tumoral Growing

After the injection of B 16F10 cells, tumoral growing was measured with a pachymeter and photo-documented daily.

Tumor longitudinal and transversal measures (two measures for each parameter) were conducted. Tumor area and average volume were calculated through the following equations: $A=\pi R^2$ and $V=4/3\pi R^3$. Animals that received tumoral cells by endovenous route were anesthetized and killed in each phase of the treatment and necropsy was conducted. The macroscopic tumoral nodules present in the internal organs were counted and measured.

Example 38

Determination of Cytotoxic Activity

The cellular viability of the cellular lineages and of tumor cells treated with different concentrations of Amblyomin-X from 0.03 nM to 0.3 uM Sodium Heparin from 80 up to 0.0015 ug, were determined by the MTT calorimetric method (3-(4,5-dimethylthiazol-2-yl) 2,5-diphenil tetrazolium bromide). The method is based on the reduction of MTT into formazan by alive cells. The determination of the sensibility to different doses of Amblyomin-X was optimized according to the standards set by the National Cancer Institute, USA (NCI). The Amblyomin-X cytotoxic activity was determined in suspensions of the cellular lineages and of the tumoral cells ("ex-vivo"), detached by surgery and in sterile conditions incubated in plates of 96 wells. To these cells 10 µl of MTT (5 mg/ml) was added and then they were incubated for 3 hours in sterilizer containing 5% of $CO_2$ at 37° C. After this period, the medium was removed and 100 µl of sulphoxide dimethyl was added for the dissolution of formazan crystals that were formed and presented as precipitated. Absorbency was monitored in 540 nm.

Example 39

Obtaining Peritoneal Macrophages

After treating mice with B16F10 melanoma and control group (that received saline solution) with Amblyomin-X, the animals were anesthetized and killed by cervical dislocation. The abdominal cavity of treated and control animals was exposed and 2 ml of saline solution containing 5000 U cool heparin was injected. The cavity was massaged and right after the peritoneal washed was collected, centrifuged in 2000 rpm for 10 minutes at 4° C. The cellular suspension was re-suspended in RPMI-1640 culture medium supplemented with bovine fetal serum 10% and the number of cells adjusted for $10^6$/ml in Mallassez haemocytometric chamber.

Aliquots of macrophages suspension were cultivated in spherical plates, previously sterilized, immersed in RPMI-1640 culture medium and maintained in plates of 12 wells incubated in presence and absence of $10^5$ Candida albicans, $10^5$ sheep erythrocytes or treated with C3Bb or with the Fc portion of the immuno-globulin. After 24 hours the plates were fixed, stained, the number of adherent cells and of phagocyte particles were counted.

Example 40

Culture of Human Skin Fibroblasts

Fragments of human skin (of approximately 1 cm×1 cm) previously selected were collected aseptically and immediately placed in a sterile conic tube containing Ham-F12 culture medium with 20% bovine fetal serum. Each fragment was transferred to a 35-mm Petri dish containing culture medium for washing and blood excess withdrawing. Fat and degenerative tissue was taken out using scissors and tongs. The "clean" fragment was cut into smaller fragments and they were then distributed in 3 Petri dishes (±15 pieces each) containing Ham-F12 culture medium supplemented with 10% of bovine fetal serum.

The plates were maintained in humidified sterilizer at 37° C. and 5% of $CO^2$ and examined in inverted microscope 3 times a week. The culture medium was exchanged in the same time interval. When they reached sub-confluence, the cells were exposed to trypsin (Trypsin 0.2%) for 5 minutes and the inactivation was conducted with bovine fetal serum 10, the cells were centrifuged for 10 minutes in 2000 rpm at 4° C. and plated in bottles of 25 cm².

After cellular growing and expansion $10^5$ fibroblasts were cultivated in plates of 96 wells for 24 hours. After that, the culture was treated with Amblyomin-X diluted in RPMI-1640 containing bovine fetal serum 10% and 7 ug/ml of polymixine-B. As control the treatment with Sodium Heparin was used in the same concentrations or with complete culture medium.

Statistical Analysis

The statistical analysis was conducted by the ANOVA Variance method followed by the TUKEY-KRAMER multiple comparative test.

Values were expressed in median±standard deviation, considering *p<0.05 as significant values.

A number of embodiments of the disclosure have been described. Nevertheless, it will be understood that various modifications may be made without departing from the spirit and scope of the disclosure. Accordingly, other embodiments are within the scope of the following claims.

REFERENCES

Available from:

www.ncbi.nlm.nih.gov/blast/network/netblast
www.ncbi.nlm.nih.gov/entrez/jrbroser.cgi
www.nlm.nih.gov/tsd/serials/lji.html
www.expasv.org
www.cbs.dtu.dk/services/sisnalP/

Barenholz Y, Gibbes D, Litman B J, Goll J, Thompson T E Carlson R D. A simple method for the preparation of homogeneous phospholipid vesicles. Biochemistry; 16(12):2806-10, 1977.

BELL, D. A.; TAYLOR, J. A.; PAULISON, D. F.; ROBERTSON, C N.; LUCIER, G. W. Genetic risk and carcinogen exposure: A common inherited defect of the carcinogen-metabolism gene glutanione S-tranferase M1 (GSTM1) that increases susceptibly to bladder cancer. J. Natl. Cancer Inst. 85: 1159-1164, 1993.

Bergqvist D. Venous thromboembolism in cancer patients: expanding horizons Semin Thromb Hemost.; 28 Suppl 3:19-23, 2002.

Broze G J Jr. Tissue factor pathway inhibitor gene disruption. Blood Coagul. Fibrinolysis Suppl. 1: S89-92, 1998.

Budillon A. Molecular genetics of cancer. Oncogenes and tumor suppressor genes. Cancer., 76(10): 1869-73, 1995.

Chand H S, Schmidt A E, Bajaj S P, Kisiel W. Structure function analysis of the reactive site in the first kunitz-type domain of human tissue factor pathway inhibitor-2. J. Biol. Chem. 23; 279 (17): 17500-7. Epub Erratum in: J Biol Chem4; 279 (23):24906, 2004

Cotrino J In situ detection of expression of tissue factor in vascular endothelial cells: correlation with the malignant phenotype of human breast disease. Nature Medicine, 2: 210-492, 1996.

DECLERCK, Y. A. & IMREM, S.—Protease inhibitors: role and potential therapeutic use in human cancer. Eur. J. Cancer, 3OA: 2170-80, 1994.

DUKE, R. C; OJCIUS, D. M.; YOUNG, J. D.-E. Cell suicide in health and disease. Scientific American, 275(6): 48-55, 1996.

Edward R L, Human Tumor Procoagulation. Thromb Haemost 69: 205-131; 1993.

FEARON, E. R. Human cancer syndromes: clues to the origin and nature of cancer. Science, 278: 1043-50, 1997.

Fernandez P M, Patierno S R, Rickles F R. Tissue factor and fibrin in tumor angiogenesis. Semin Thromb Hemost; 30 (1): 31-44, 2004

Gale A J, Gordon S G. Update on tumor cell procoagulant factors. Acta Haematol; 106 (1-2):25-32, 2001

Goel H L, Languino L R. Integrin signaling in cancer. Cancer Treat Res.; 119: 15-31, 2004.

Gordon S G: Cancer cell pro coagulants and their implications. Hematol Oncol Clin North Am. 6: 1539-74,1992.

Gouin-Thibaut I, Samama M M. Venous thrombosis and cancer. Ann Biol Clin 58 (6): 675-82, 2000.

GREAVES, M. Dying for a living. In: Cancer the evolutionary legacy. Oxford University Press, 196-203, 2000.

Hermo H Jr., Chemical carcinogenesis: tumor initiation and promotion. Occup Med., 2(1): 1-25, 1987.

Hoffman R, Haim N, Brenner B. Cancer and thrombosis revisited. Blood Rev.; 15 (2): 61-7, 2001.

Kamei S, Petersen L C, Sprecher C A, Foster D C, Kisiel W. Inhibitory properties of human recombinant Arg24→Gln type-2 tissue factor pathway inhibitor (R24Q TFPI-2). Thromb Res. 1; 94 (3):147-52, 1999.

Lee A Y, Levine M N. Venous thromboembolism and cancer: risks and outcomes. Circulation 17; 107(23 Suppl 1):I17-21, 2003.

Loreto M F, De Martinis M, Corsi M P, Modesti M, Ginaldi L. Coagulation and cancer: implications for diagnosis and management. Pathol Oncol Res; 6 (4): 301-12, 2000.

Matsuda A, Suzuki Y, Honda G, Muramatsu S, Matsuzaki O, Nagano Y, Doi T, Shimotohno K, Harada T, Nishida E, Hayashi H, Sugano S. Large-scale identification and characterization of human genes that activate NF-kappaB and MAPK signaling pathways. Oncogene; 22(21): 3307-18, 2003.

MEYER, T.; HART, I. R. Mechanisms of tumor metastasis. European Journal of Cancer, 34 (2): 214-221, 1998.

Moussa S A. Antithrombotics in thrombosis and cancer, Expert Rev Cardiovasc Ther., 1(2): 283-91, 2003

Ornstein D L, Zacharski L R Cancer, thrombosis, and anticoagulants. Curr Opin Pulm Med., 6 (4): 301-8, 2000.
Rao L V, Ruf W. Tissue factor residues Lyslβ∆ and Lyslββ are essential for rapid formation of the quaternary complex of tissue factor.Vila with Xa.tissue factor pathway inhibitor. Biochemistry; 34 (34): 10867-71, 1995.
Ribeiro, J. M. C. Blood-feeding arthropods: live syringes or invertebrate pharmacologists? Infect Agents Dis.; 4 (3): 143-52, 1995.

Rickels F: Hemostatic alterations in cancer patients. Cancer Metat. Rev 11: 239; 1992.

RUOSLAHTI, E. How cancer spreads. Scientific American, 275 (3): 72-77, 1996.

Sandset P M, Bendz B. Tissue factor pathway inhibitor: clinical deficiency states. Thromb Haemost; 78 (1): 467-70, 1997

Schafer A I, Levine M N, Konkle B A, Kearon C. Thrombotic disorders: diagnosis and treatment Hematology (Am Soc Hematol Educ Program); 520-39, 2003

Sekine I, Yamamoto N, Kunitoh H, Ohe Y, Tamura T, Kodama T, Saijo N. Cancer Treatment of small cell lung cancer in the elderly based on a critical literature review of clinical trials. Cancer Treat Rev.,-30 (4): 359-68, 2004
Sorensen B B, Rao L V, Tomehave D, Gammeltoft S, Petersen L C. Antiapoptotic effect of coagulation factor Vila. Blood. 102(5): 1708-15, 2003.
Sorensen H T, Johnsen S P, Norgard B, Zacharski L R, Baron J A. Cancer and venous thromboembolism: a multidisciplinary approach. Clin Lab.; 49 (11-12): 615-23, 2003.

Sutherland D E, Weitz I C, Liebman H A. Thromboembolic complications of cancer: epidemiology, pathogenesis, diagnosis, and treatment. Am J Hematol; 72 (1): 43-52, 2003.

Tsao A S, Kim E S, Hong W K. CA Chemoprevention of cancer. CA Cancer J. Clin./54(3): 150-80, 2004.

Wainscoat J S, Fey M F. Assessment of clonality in human tumors: a review. Cancer Res. 50 (5): 1355-60, 1990.

Zacharski L R, Pathways of coagulation, fibrinolysis activation in malignancy. Semin Thromb Hemostasis 18: 104; 1992.

Zacharski L R. Malignancy as a solid-phase coagulopathy: implications for the etiology, pathogenesis, and cancer treatment. Semin Thromb Hemost. 29(3) 317-320, 2003.

What is claimed is:

1. A purified polypeptide comprising the amino acid sequence of SEQ ID NO:2.

2. The polypeptide of claim 1, wherein the polypeptide comprises an activity selected from the group consisting of:
   (i) decreasing FXa-mediated blood coagulation, wherein the decrease occurs in the presence of phospholipids;
   (ii) promoting apoptosis of B16F10 cells;
   (iii) promoting apoptosis of SKMEL28 cells;
   (iv) decreasing tumor mass in a C57BL/6J mouse implanted with B16F10 tumor cells;
   (v) decreasing tumor metastasis in a C57BL/6J mouse implanted with B16F10 tumor cells;
   (vi) decreasing angiogenesis in a C57BL/6J mouse implanted with B16F10 tumor cells; and
   (vii) increasing macrophage phagocytic activity in a C57BL/6J mouse implanted with B16F10 tumor cells.

3. A purified polypeptide consisting of the amino acid sequence of SEQ ID NO:2.

4. A purified polypeptide comprising the amino acid sequence of SEQ ID NO:3.

5. The polypeptide of claim 4, wherein the polypeptide comprises an activity selected from the group consisting of:
   (i) decreasing FXa-mediated blood coagulation, wherein the decrease occurs in the presence of phospholipids;
   (ii) promoting apoptosis of B16F10 cells;
   (iii) promoting apoptosis of SKMEL28 cells;
   (iv) decreasing tumor mass in a C57BL/6J mouse implanted with B16F10 tumor cells;
   (v) decreasing tumor metastasis in a C57BL/6J mouse implanted with B16F10 tumor cells;
   (vi) decreasing angiogenesis in a C57BL/6J mouse implanted with B16F10 tumor cells; and
   (vii) increasing macrophage phagocytic activity in a C57BL/6J mouse implanted with B16F10 tumor cells.

6. A purified polypeptide consisting of the amino acid sequence of SEQ ID NO:3.

7. A purified polypeptide comprising amino acids 1-61 of SEQ ID NO:3, wherein the polypeptide comprises an activity selected from the group consisting of:
   (i) decreasing FXa-mediated blood coagulation, wherein the decrease occurs in the presence of phospholipids;
   (ii) promoting apoptosis of B16F10 cells;
   (iii) promoting apoptosis of SKMEL28 cells;
   (iv) decreasing tumor mass in a C57BL/6J mouse implanted with B16F10 tumor cells;
   (v) decreasing tumor metastasis in a C57BL/6J mouse implanted with B16F10 tumor cells;
   (vi) decreasing angiogenesis in a C57BL/6J mouse implanted with B16F10 tumor cells; and
   (vii) increasing macrophage phagocytic activity in a C57BL/6J mouse implanted with B16F10 tumor cells.

8. A purified polypeptide comprising amino acids 62-108 of SEQ ID NO:3, wherein the polypeptide comprises an activity selected from the group consisting of:
   (i) decreasing FXa-mediated blood coagulation, wherein the decrease occurs in the presence of phospholipids;
   (ii) promoting apoptosis of B16F10 cells;
   (iii) promoting apoptosis of SKMEL28 cells;
   (iv) decreasing tumor mass in a C57BL/6J mouse implanted with B16F10 tumor cells;
   (v) decreasing tumor metastasis in a C57BL/6J mouse implanted with B16F10 tumor cells;
   (vi) decreasing angiogenesis in a C57BL/6J mouse implanted with B16F10 tumor cells; and
   (vii) increasing macrophage phagocytic activity in a C57BL/6J mouse implanted with B16F10 tumor cells.

9. A pharmaceutical composition comprising the polypeptide of claim 1.

10. A pharmaceutical composition comprising the polypeptide of claim 4.

11. A method of decreasing blood coagulation in a subject, the method comprising administering the polypeptide of claim 1 to the subject.

12. A method of treating cancer in a subject, the method comprising administering the polypeptide of claim 1 to the subject.

13. The method of claim 12, wherein the polypeptide is administered with a chemotherapy treatment.

14. The method of claim 12, wherein the polypeptide is administered with a radiotherapy treatment.

15. A method of decreasing tumor progression in a subject, the method comprising administering the polypeptide of claim 1 to the subject.

16. A method of decreasing tumor metastasis in a subject, the method comprising administering the polypeptide of claim 1 to the subject.

17. A method of decreasing tumor angiogenesis in a subject, the method comprising administering the polypeptide of claim 1 to the subject.

18. A method of increasing phagocytic activity in a subject, the method comprising administering the polypeptide of claim 1 to the subject.

19. A method of treating, reducing, or inhibiting a thromboembolism in a subject, the method comprising administering the polypeptide of claim 1 to the subject.

20. The method of claim 19, wherein the method is performed in a pre- or post-operative setting.

21. A method of decreasing blood coagulation in a subject, the method comprising administering the polypeptide of claim 4 to the subject.

22. A method of treating cancer in a subject, the method comprising administering the polypeptide of claim 4 to the subject.

23. The method of claim 22, wherein the polypeptide is administered with a chemotherapy treatment.

24. The method of claim 22, wherein the polypeptide is administered with a radiotherapy treatment.

25. A method of decreasing tumor progression in a subject, the method comprising administering the polypeptide of claim 4 to the subject.

26. A method of decreasing tumor metastasis in a subject, the method comprising administering the polypeptide of claim 4 to the subject.

27. A method of decreasing tumor angiogenesis in a subject, the method comprising administering the polypeptide of claim 4 to the subject.

28. A method of increasing phagocytic activity in a subject, the method comprising administering the polypeptide of claim 4 to the subject.

29. A method of treating, reducing, or inhibiting a thromboembolism in a subject, the method comprising administering the polypeptide of claim 4 to the subject.

30. The method of claim 29, wherein the method is performed in a pre- or post-operative setting.

31. A purified polypeptide comprising an amino acid sequence that is at least 85% identical to the amino acid sequence of SEQ ID NO:2, wherein the polypeptide comprises an activity selected from the group consisting of:
(i) decreasing FXa-mediated blood coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

32. The purified polypeptide of claim 31 comprising an amino acid sequence that is at least 95% identical to the amino acid sequence of SEQ ID NO:2, wherein the polypeptide comprises an activity selected from the group consisting of:
(i) decreasing FXa-mediated blood coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

33. The purified polypeptide of claim 31 comprising an amino acid sequence that is at least 99% identical to the amino acid sequence of SEQ ID NO:2, wherein the polypeptide comprises an activity selected from the group consisting of:
(i) decreasing FXa-mediated blood coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

34. A purified polypeptide comprising an amino acid sequence that is at least 85% identical to the amino acid sequence of SEQ ID NO:3, wherein the polypeptide comprises an activity selected from the group consisting of:
(i) decreasing FXa-mediated blood coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

35. The purified polypeptide of claim 34 comprising an amino acid sequence that is at least 95% identical to the amino acid sequence of SEQ ID NO:3, wherein the polypeptide comprises an activity selected from the group consisting of:
(i) decreasing FXa-mediated blood coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

36. The purified polypeptide of claim 34 comprising an amino acid sequence that is at least 99% identical to the amino acid sequence of SEQ ID NO:3, wherein the polypeptide comprises an activity selected from the group consisting of:
(i) decreasing FXa-mediated blood coagulation, wherein the decrease occurs in the presence of phospholipids;
(ii) promoting apoptosis of B16F10 cells;
(iii) promoting apoptosis of SKMEL28 cells;
(iv) decreasing tumor mass in a C57BL/6J mouse implanted with B16F10 tumor cells;
(v) decreasing tumor metastasis in a C57BL/6J mouse implanted with B16F10 tumor cells;
(vi) decreasing angiogenesis in a C57BL/6J mouse implanted with B16F10 tumor cells; and
(vii) increasing macrophage phagocytic activity in a C57BL/6J mouse implanted with B16F10 tumor cells.

\* \* \* \* \*

UNITED STATES PATENT AND TRADEMARK OFFICE
CERTIFICATE OF CORRECTION

PATENT NO. : 8,440,795 B2
APPLICATION NO. : 11/724557
DATED : May 14, 2013
INVENTOR(S) : Durvanei Augusto Maria et al.

It is certified that error appears in the above-identified patent and that said Letters Patent is hereby corrected as shown below:

Title Page, Item (73) (Assignee), Line 1, delete "Confair-Consórcio" and insert
-- Coinfar-Consórcio --.

Title Page, Item (30) (Foreign Application Priority Data), Line 1, delete "0406057" and insert -- PI0406057-1 --.

Signed and Sealed this
Twentieth Day of August, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,440,795 B2 | Page 1 of 1 |
| APPLICATION NO. | : 11/724557 | |
| DATED | : May 14, 2013 | |
| INVENTOR(S) | : Maria et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 795 days.

Signed and Sealed this
Ninth Day of December, 2014

Michelle K. Lee
*Deputy Director of the United States Patent and Trademark Office*